United States Patent [19]

Yamanaka et al.

[11] Patent Number: 5,444,083

[45] Date of Patent: Aug. 22, 1995

[54] PYRROLIDINE COMPOUND AND PHARMACEUTICAL USE

[75] Inventors: Motosuke Yamanaka, Chiba; Tomonori Hoshiko, Ibaraki; Shinji Suda, Ibaraki; Naoki Yoneda, Ibaraki; Nobuyuki Mori, Ibaraki; Mitsumasa Shino, Ibaraki; Hiroki Ishihara, Ibaraki; Mamoru Saito, Ibaraki; Toshiyuki Matsuoka, Ibaraki, all of Japan

[73] Assignee: Eisai Co., Ltd., Japan

[21] Appl. No.: 468,147

[22] Filed: Jan. 22, 1990

[30] Foreign Application Priority Data

Feb. 3, 1989 [JP] Japan .................................. 1-25262
Sep. 29, 1989 [JP] Japan ................................. 1-254349

[51] Int. Cl.⁶ ..................... A61K 31/40; C07D 207/08
[52] U.S. Cl. .................... 514/429; 546/275; 548/314.7; 548/527; 548/577
[58] Field of Search ................. 548/577; 514/429

[56] References Cited

U.S. PATENT DOCUMENTS 2,852,526  9/1958  Villani et al. ................ 548/543 X

FOREIGN PATENT DOCUMENTS 232503   8/1963  Austria .
0071399  2/1983  European Pat. Off. .
3025436  1/1981  Germany .

*Primary Examiner*—Joseph Paul Brust
*Attorney, Agent, or Firm*—Birch, Stewart, Kolasch & Birch

[57] ABSTRACT

A pyrrolidine compound having the following formula and a pharmacologically acceptable salt thereof is disclosed. It is useful in the pharmaceutical field.

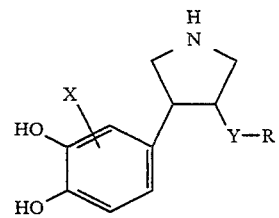

in which X is hydrogen, a halogen, or a lower alkyl, Y is —(CH2)n—, n being zero, 1 or 2, —S(O)p—, p being zero, 1 or 2, —O—, or —NH— and R is phenyl, a substituent-having phenyl, naphtyl, a substituent-having naphthyl, a heteroaryl or a substituent-having heteroaryl.

15 Claims, No Drawings

PYRROLIDINE COMPOUND AND PHARMACEUTICAL USE

BACKGROUND OF THE INVENTION

The present invention relates to a pyrrolidine derivative and a pharmacologically acceptable salt thereof which exhibits excellent pharmaceutical activities.

About 20% of the Japanese at large, i.e., about 20 million or more Japanese are suffering from hypertension which is an important risk factor of various cerebral diseases, cardiac diseases, etc. At the present time, hypotensive and diuretic agents, β-blockers, Ca antagonists, ACE inhibitors, etc. are actually used for clinical purposes in the pharmacotherapy for hypertension.

However, there are a wide variety of origins and pathological conditions on the hypertension, and it is very difficult to significantly control all the types of hypertensions with only one drug. Further, with respect to safety, for example, the β-blocker exhibits side effects such as cardiac depression and bronchoconstriction, while the diuretic agent exhibits side effects such as hyperuricemia, saccharometabolism disorder, and lipid metabolism disorder.

Under these circumstances, better hypotensive drugs different from one another in the mechanism of action have been still desired.

In view of the above, the present inventors have made extensive and intensive studies for years particularly on a dopamine 1 agonist with a view to developing a hypotensive drug, particularly one having a renal blood flow increasing activity and, as a result, have found that a pyrrolidine derivative which will be described hereinbelow exhibits an excellent activity.

Pyrrolidine derivatives having a hypotensive activity are scarcely known in the art.

Although U.S. Pat. No. 2,852,526 discloses a pyrrolidine derivative, this compound is different from the compound of the invention in chemical structure and remarkably different also in the pharmaceutical effect, as is apparent from the fact that the U.S. Patent describes only that the compound exhibits bronchodilator, antihistaminic, and anticholinergic activities.

Although Fenoldopam (SKF-82526) has been proposed as a compound having a renal blood flow increasing activity, this compound is a benzazepine compound and different from the compound of the present invention in the structure.

SUMMARY OF THE INVENTION

The invention provides a pyrrolidine compound having the following formula and a pharmacologically acceptable salt thereof.

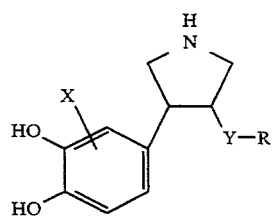

(I)

in which X is hydrogen, a halogen, or a lower alkyl, Y is —(CH2)n—, n being zero, 1 or 2, —S(O)p—, p being zero, 1 or 2, —O—, or —NH— and R is phenyl, a substituent-having phenyl, naphthyl, a substituent-having naphthyl, a heteroaryl or a substituent-having heteroaryl.

The compound is preferably to be in the trans-form.

It is preferable that in the formula Y is —(CH2)n— and n is zero.

R may preferably have the formula:

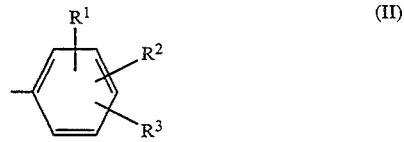

(II)

in which $R^1$, $R^2$ and $R^3$ are each hydrogen, a lower alkyl, a lower alkoxy, a halogen, hydroxy, trifluoromethyl or —NR4R5, $R^4$ and $R^5$ are each hydrogen or a lower alkyl.

$R^1$, $R^2$ and $R^3$ are each preferred to be hydrogen, a halogen, hydroxy or a lower alkyl.

It is preferable that R is phenyl or a substituted phenyl, a substituent being selected from a lower alkyl, trifluoromethyl, a halogen and hydroxy.

R for the heteroaryl is preferred to be thienyl or a substituent-having thienyl such as a thienyl having a lower alkyl or hydroxy.

A preferable compound is 3-(2-chloro-3-hydroxyphenyl)-4-(3,4-dihydroxyphenyl)-pyrrolidine, in particular (+)-trans-3-(2-chloro-3-hydroxyphenyl)-4-(3,4-dihydroxyphenyl)-pyrrolidine and (-)-trans-3-(2-chloro-3-hydroxyphenyl)-4-(3,4-dihydroxyphenyl)-pyrrolidine.

Further preferable compounds are listed below. These are more useful in the trans-form.

3-(3,4 -dihydroxyphenyl)-4-(2-methylphenyl)pyrrolidine 3-(2 -chlorophenyl)-4-(3,4-dihydroxyphenyl)pyrrolidine 3-(2-chloro-3-hydroxyphenyl)-4- (3,4-dihydroxyphenyl)pyrrolidine 3-(3,4-dihydroxyphenyl)-4-(3-methylthienyl)pyrrolidine hydrobromide (3,4-dihydroxyphenyl)-4-(3-methylthienyl)pyrrolidine 3-(7-benzothiophenyl)-4-(3,4-dihydroxyphenyl)pyrrolidine 3-(3-chloro-6-hydroxyphenyl)-1-methyl-4-(3,4-dihydroxyphenyl)-pyrrolidine 3-(2,6-dihydroxyphenyl)methyl-4-(3,4-dihydroxyphenyl)pyrrolidine 3-(3-chloro-2,6-dihydroxyphenyl)-methyl-4-(3,4-dihydroxyphenyl)pyrrolidine 3-(3,5-difluoro-2-hydroxyphenyl)-methyl-4-(3,4-dihydroxyphenyl)-pyrrolidine 3-(3-fluoro-2-hydroxyphenyl)methyl-4-(3,4-dihydroxyphenyl)pyrrolidine The invention further provides a pharmaceutical composition which comprises a therapeutically effective amount of the compound or the salt as defined above and a pharmacologically acceptable carrier. The composition is to use for the treatment or prevention of a disease for which dopamine 1 agonist activity is effective, then for the treatment or prevention of hypertension and for the treatment or prevention of heart failure.

In addition the invention provides a dopamine 1 agonist comprising the compound or the salt as defined above.

The invention further relates to a method for treating or preventing a disease for which dopamine 1 agonist activity is effective, which comprises administering to a patient suffering from said disease a therapeutically or preventively effective amount of the compound or the salt as defined above, a method for treating or preventing hypertension, which comprises administering to a patient suffering from the hypertension a therapeutically or preventively effective amount of the compound or the salt as above and a method for treating or preventing heart failure, which comprises administering to a patient suffering from the heart failure a therapeutically or preventively effective amount of the compound or the salt as defined above.

The term "lower alkyl group" used in the above definition of X for the compound (I) of the present invention and in the above definition of $R^1$, $R^2$, $R^3$, $R^4$, and $R^5$ of the group represented by the above formula (II) is intended to mean a straight-chain or branched alkyl group having 1 to 6 carbon atoms, and examples thereof include methyl, ethyl, n-propyl, n-butyl, isopropyl, isobutyl, 1-methylpropyl, tert-butyl, n-pentyl, 1-ethylpropyl, isoamyl, and n-hexyl. Examples of the most desirable lower alkyl group include methyl and ethyl groups.

The term "halogen atom" used in the above definition of X in the formula (I) and in the above definition of $R^1$, $R^2$, and $R^3$ in the formula (II) is intended to mean chlorine, iodine, bromine, or fluorine.

The term "lower alkoxy group" used in the definition of $R^1$, $R^2$, and $R^3$ is intended to mean a lower alkoxy group derived from the above-described lower alkyl group, and preferable examples thereof include methoxy and ethoxy groups.

The term "substituted naphthyl group" used in the definition of R is preferably intended to mean a naphthyl group preferably substituted by a lower alkyl group represented by methyl and ethyl groups, a lower alkoxy group represented by methoxy and ethoxy groups, a halogen atom, a hydroxyl group, a trifluoromethyl group, or the like.

The term "heteroaryl group" used in the definition of R is intended to mean a substituted or unsubstituted heterocyclic group. The heterocyclic group may contain one or more nitrogen, oxygen, or sulfur atoms. Specific examples thereof include imidazolyl groups such as 1-imidazolyl and 2-imidazolyl groups, pyridyl groups such as 3-pyridyl and 4-pyridyl groups, pyrrolyl groups such as 1-pyrrolyl group and 3-pyrrolyl groups, nitrogen atom-containing heteroaryl groups such as pyrazolyl, indolyl, indazolyl, isoquinolyl, quinolyl, quinoxalinyl, quinazolinyl and imidazopyridyl groups, heteroaryl groups containing oxygen atom besides nitrogen atom such as oxazolyl and isoxazolyl groups, and sulfur atom-containing heteroaryl groups derived from thiophene and benzothiophene. The most desirable examples thereof include pyridyl, imidazolyl, thienyl

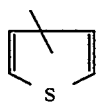

and benzothiophenyl.

The above heteroaryl group may be substituted by a lower alkyl group such as a methyl or ethyl group, a lower alkoxy group such as a methoxy or ethoxy group, a halogen atom, or the like.

Preferred examples of the compound (I) of the present invention include those wherein R is a group represented by the formula (II), i.e., those represented by the following general formula (III):

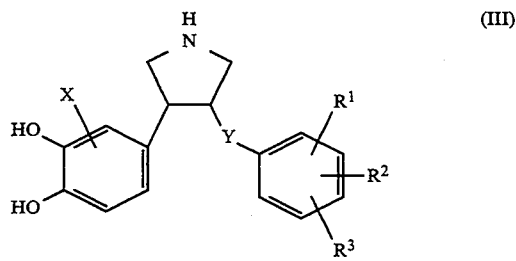

in which X, $R^1$, $R^2$ and $R^3$ are defined above, Y is —$(CH_2)_n$— and n is zero.

In the above-described general formula (III), X is most desirably a hydrogen atom, and $R^1$, $R^2$ and $R^3$ are each preferably hydrogen, a lower alkoxy, a halogen, hydroxy and trifluoromethyl.

The above compound is still preferably one having two substituents, i.e., a halogen atom and a hydroxyl group. In this case, substitution with a hydroxyl group in the m-position and with a halogen atom, such as a chlorine atom, in the o-position is most desirable.

Additional preferred examples of the compound include those wherein R is a heteroaryl group.

In the present invention, examples of the pharmacologically acceptable salt include salts of inorganic acids, such as hydrochloride, sulfate, hydrobromide, and phosphate, and those of organic acids, such as formate, acetate, trifluoroacetate, maleate, fumarate, tartrate, methanesulfonate, benzenesulfonate, toluenesulfonate and a metal salt thereof such as that with sodium and potassium.

Some compounds may form hydrates, and it is needless to say that these hydrates may fall within the scope of the present invention.

As is apparent from the chemical structure, the compound of the present invention may be present in the form of various isomers. Specifically, it may be present as positional isomers, such as cis from and trans form, besides optically active d and l isomers. It is needless to say that these isomers fall within the scope of the present invention.

In the present invention, the trans form is preferred among stereoisomers.

The compound of the present invention exhibits significant hypotensive and renal blood flow increasing activities. Since the compound of the present invention has a high affinity for dopamine 1 receptor and stimulates the same, it has hypotensive, renal blood flow increasing, and diuretic activities based on the vasodilator action which are desirable as a antihypertensive drug and further has excellent safety.

The compound of the present invention has hypotensive, renal blood flow increasing and diuretic activities based on the vasodilator action which are desirable as a antihypertensive drug and further has excellent safety, which renders the compound of the present invention favorable as a hypotensive drug or a therapeutic agent for heart failure.

Therefore, the compound of the present invention is useful as therapeutic and preventive agents for various hypertensions such as essential hypertension and renal hypertension and further therapeutic and preventive agents for heart failure.

When the compounds of the present invention are used as the above-described drugs, they may be either orally or parenterally administered. The dosage will remarkably vary depending upon the symptom; age, sex, weight, and sensitivity of patients; method of administration; time and intervals of administration and properties, formulation, and kind of pharmaceutical preparations; kind of active ingredients, etc., so that there is no particular limitation on the dosage.

In the case of oral administration, the dosage may be about 1 to 1,000 mg, preferably about 50 to 600 mg, still preferably about 150 to 400 mg, further preferably about 300 to 400 mg per day per adult ordinarily in one to four portions. In the case of injection, the dosage is usually about 0.3 to 100 μg/kg, preferably about 1 to 10 μg/kg.

In preparing a solid preparation for oral administration, the active ingredient is blended with a vehicle and, if necessary, a binder, a disintegrator, a lubricant, a colorant, a corrigent, etc., and tablets, coated tablets, granules, powders, capsules, etc. are prepared therefrom by a customary method.

Examples of the vehicle include lactose, corn starch, sucrose, glucose, sorbitol, crystalline cellulose, and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin, and pectin. Examples of the lubricant include magnesium stearate, talc, polyethylene glycol, silica, and hydrogenated vegetable oil. Any colorant of which the addition to pharmaceuticals is officially allowed can be used as the colorant. Examples of the corrigent include cacao powder, menthol, aromatic acid, mentha oil, camphor, and powdered cinnamon bark. It is a matter of course that a sugar coating, a gelatin coating and, if necessary, suitable other coatings may be applied on these tablets and granules.

In preparing injections, the active ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to any ordinary method.

Examples of the suspending agent include methylcellulose, Polysorbate 80, hydroxyethylcellulose, gum arabic, powdered tragacanth, sodium carboxymethylcellulose, and polyoxyethylene sorbitan monolaurate.

Examples of the solubilizing agent include polyoxyethylene hydrogenated castor oil, Polysorbate 80, nicotinamide, polyoxyethylene sorbitan monolaurate, Macrogol, and ethyl esters of castor oil fatty acids.

Examples of the stabilizer include sodium sulfite, sodium metasulfite, and ether, and examples of the preservative include methyl p-hydroxybenzoate, ethyl p-hydroxybenzoate, sorbic acid, phenol, cresol, and chlorocresol.

The compound of the invention includes the two embodiments which are each explained below.

The compound of the present invention is a pyrrolidine derivative and a pharmacologically acceptable salt thereof represented by the following general formula (I):

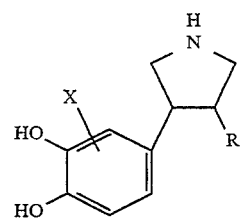

wherein X is a hydrogen atom, a halogen atom, or a lower alkyl group and R is a substituted or unsubstituted phenyl group, a substituted or unsubstituted naphthyl group, or a heteroaryl group.

A representative process for preparing the compounds of the present invention will now be described.

<Preparation Process 1>

Although the compound of the present invention may be present in both the trans and cis forms as described above, the preparation of the trans form will now be described.

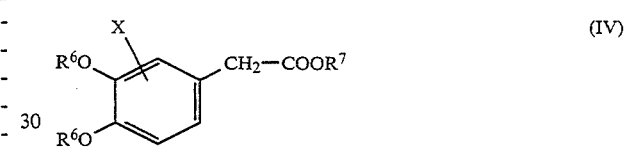

(IV)

(V)

step 1
(addition)

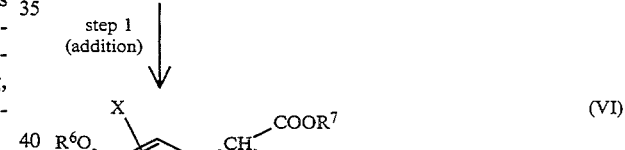

(VI)

step 2
(reduction)

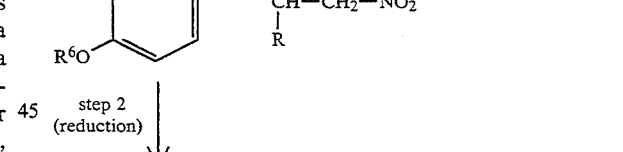

(VII)

step 3
(cyclization)

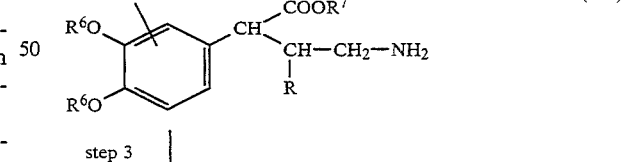

(VIII)

step 4
(isomerization)

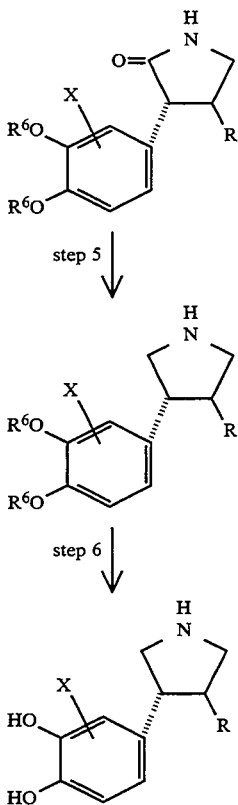

wherein X and R are each as defined above, $R^7$ is a lower alkyl group and $R^6$ is a protective group for a hydroxyl group.

(Step 1)

In this step, a derivative of a lower alkyl phenylacetate represented by the general formula (IV) is reacted with a β-nitroarylethene represented by the general formula (V) to prepare a compound represented by the general formula (VI).

This reaction is conducted by a customary method. For example, the reaction is conducted by making use of an ether solvent such as diethyl ether, tetrahydrofuran or diglyme, a hydrocarbon solvent such as benzene or toluene, or other solvents such as N,N-dimethylformamide or dimethyl sulfoxide in the presence of a base.

A specific example of preferred reaction methods comprises producing lithium diisopropylamide from n-butyllithium and diisopropylamine at a low temperature in tetrahydrofuran, adding a solution of a compound represented by the general formula (IV) in tetrahydrofuran to the reaction product, and conducting a reaction of the resultant mixture with a solution of a compound represented by the general formula (V) in tetrahydrofuran.

In the general formula (IV), $R^6$ represents a protective group for a hydroxyl group. It may be any group so long as it can protect a hydroxyl group. Representative examples thereof include lower alkyl groups such as methyl, ethyl, propyl and butyl, aralkyl groups such as benzyl and phenethyl, acyl groups such as acetyl, propionyl, butyroyl and pivaloyl, and a tetrahydropyranyl group. Further, two $R^6$ groups may be combined together to form an alkylene group such as a methylene group.

Among them, a lower alkyl group, such as a methyl or ethyl group, or a methylene group (which finally forms a methylenedioxy group) formed by combining two $R^6$ groups together is most desirable. In the reaction of step 1, a compound represented by the general formula (VI) can be prepared by conducting the same reaction as that adescribed above by making use of the following compound as the starting substance:

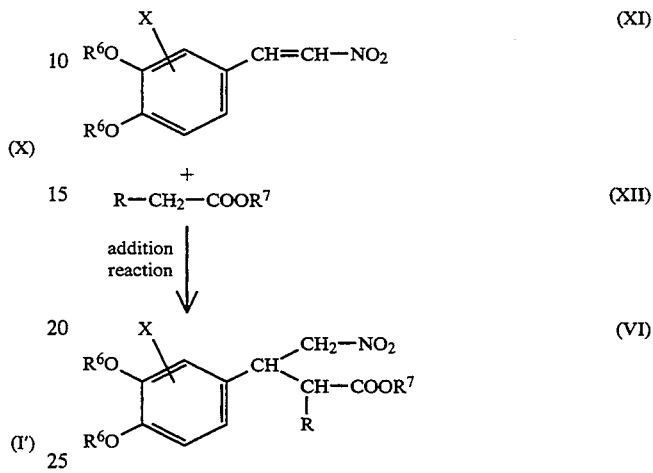

wherein $R^6$, $R^7$, X, and R are as defined above.

(Step 2)

In this step, a nitro compound represented by the general formula (VI) is reduced with metal and metallic salt, or catalytically reduced to prepare an amino compound represented by the general formula (VII). Zinc, iron, stannous chloride, etc. are used as the metal and metallic salt, while palladium/carbon, platinum oxide, Raney nickel, etc. are used as the catalyst for the catalytic reduction.

(Step 3)

In this step, a compound represented by the general formula (VII) is cyclized by heating or warming in the absence of any solvent or in the presence of a commonly employed organic solvent to prepare a five-membered lactam represented by the general formula (VIII). This reaction is usually conducted in an alcohol solvent such as methanol, ethanol or butanol, an alkyl halide solvent such as dichloromethane, chloroform, dibromoethane or dichloroethane, a hydrocarbon solvent such as benzene, toluene or xylene, an ether solvent such as tetrahydrofuran or diglyme, or other solvents such as N,N-dimethylformamide or dimethyl sulfoxide.

When the reduction of the nitro group in step 2 is conducted at a high temperature, optionally in an autoclave, a cyclized compound (VIII) can be prepared without isolation of the compound (VII).

(Step 4)

In this step, a mixture of a five-membered lactam in the cis form with a five-membered lactam in the trans form each represented by the general formula (VIII) is heated in the presence or absence of a base in an organic solvent to isomerize the cis lactam, thereby obtaining only the trans lactam represented by the general formula (IX). A preferred example of the reaction methods is one wherein the reaction is conducted by heating the mixture either in ethanol or a mixed solvent comprising ethanol and xylene in the presence of potassium tert-butoxide, or in xylene in the presence of potassium trimethylsilanolate.

(Step 5)

In this step, the trans five-membered lactam represented by the general formula (IX) is reduced with diborane or a metal-hydrogen complex compound to prepare a pyrrolidine derivative represented by the general formula (X). Preferred metal-hydrogen complex compounds include aluminum lithium hydride and bis(2-methoxyethoxy)aluminum sodium hydride, and the reduction is conducted in an ether solvent such as ether, tetrahydrofuran or diglyme, or an aromatic hydrocarbon solvent such as benzene, toluene or xylene. (Step 6)

In this step, the compound represented by the general formula (X) is treated with boron tribromide, boron trichloride, hydrobromic acid, hydriodic acid, or any other agent which causes ether linkage cleavage to remove the protective group, thereby preparing a compound represented by the general formula (I').

<Preparation Process 2>

The cis form of the compound of the present invention can be prepared by, e.g., treating the adduct represented by the general formula (VI) and obtained in step 1 of Process 1, or the amino ester (VII) obtained in step 2 of Process 1 by silica gel column chromatography to isolate a desired isomer and then conducting the same procedure as that of Process 1 (except for step 4).

<Preparation Process 3>

The compound represented by the general formula (I) contains optically active d and l isomers besides the positional isomers of cis and trans forms. Resolution of the optical isomers is conducted by an ordinary method, and examples thereof include a method wherein the mixture is passed through a column for separating optical isomers, such as a chiral column, and a method wherein the isomers are separated in the form of a salt with an optically active acid, such as (+)-tartaric acid, (+)-camphoric acid, (+)-dibenzoyl tartrate, (+)-10-camphorsufonic acid, or (+)-mandelic acid from a suitable solvent by fractional crystallization. Its (−) form may be used.

The optically active substance represented by the general formula (I) can be obtained by subjecting the compound represented by the general formula (X) or a derivative thereof to optical resolution in the same method as that described above and then conducting the reaction of step 6.

The compound of the present invention is a pyrrolidine derivative and a pharmacologically acceptable salt thereof represented by the following general formula (I):

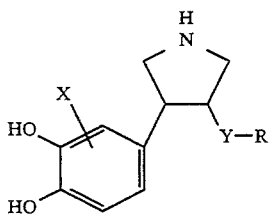
(I)

wherein X is a hydrogen atom, a halogen atom, or a lower alkyl group, Y is a group represented by the formula —(CH$_2$)$_n$— wherein n is an integer of 1 or 2, a group of the formula

wherein p is 0 or an integer of 1 or 2, a group represented by the formula —O—, or a group represented by the formula —NH—, and R is a substituted or unsubstituted phenyl group, a substituted or unsubstituted naphthyl group, or a heteroaryl group.

A representative process for preparing the compounds of the present invention will now be described.

<Preparation Process 1>

Although the compound of the present invention may be present in both the trans and cis forms as described above, the preparation of the trans form will now be described.

(IV)

(V)

step 1
(addition)

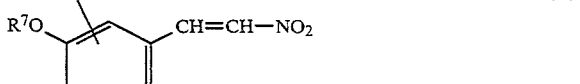
(VI)

step 2
(reduction)

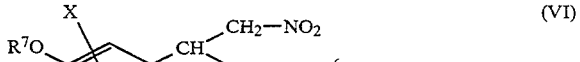
(VII)

step 3
(cyclization)

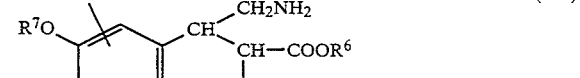
(VIII)

step 4
(isomerization)

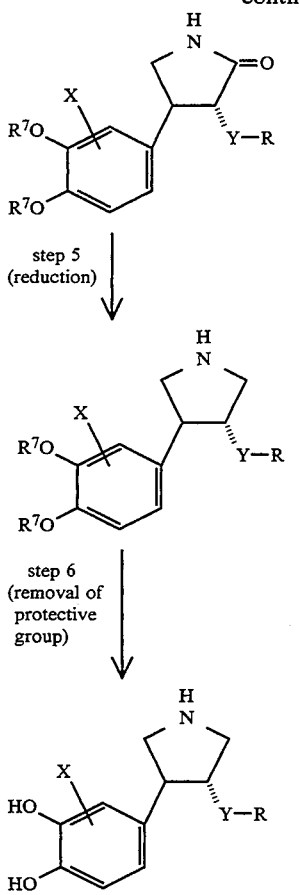

step 5
(reduction)

step 6
(removal of protective group)

wherein X, Y and R are each as defined above, $R^6$ is a lower alkyl group and $R^7$ is a protective group for a hydroxyl group.

(Step 1)

In this step, a compound represented by the general formula (IV) is reacted with a β-nitroaryl-ethane represented by the general formula (V) to prepare a compound represented by the general formula (VI).

This reaction is conducted by a customary method. For example, the reaction is conducted by making use of an ether solvent such as diethyl ether, tetrahydrofuran or diglyme, a hydrocarbon solvent such as benzene or toluene, or other solvents such as N,N-dimethylformamide or dimethyl sulfoxide in the presence of a base.

A specific example of preferred reaction methods comprises producing lithium diisopropylamide from n-butyllithium and diisopropylamine at a low temperature in tetrahydrofuran, adding a solution of a compound represented by the general formula (IV) in tetrahydrofuran to the reaction product, and conducting a reaction of the resultant mixture with a solution of a compound represented by the general formula (V) in tetrahydrofuran.

In the general formula (V), $R^7$ represents a protective group for a hydroxyl group. It may be any group so long as it can protect a hydroxyl group. Representative examples thereof include lower alkyl groups such as methyl, ethyl, propyl and butyl, aralkyl groups such as benzyl and phenethyl, acyl groups such as acetyl, propionyl, butyroyl and pivaloyl, and tetrahydropyranyl group. Further, two $R^7$ groups may be combined together to form an alkylene group such as a methylene group.

Among them, a lower alkyl group, such as a methyl or ethyl group, or a methylene group (which finally forms a methylenedioxy group) formed by combining two $R^7$ groups together is most desirable.

(Step 2)

In this step, a nitro compound represented by the general formula (VI) is reduced with metal and metallic salt, or catalytically reduced to prepare an amino compound represented by the general formula (VII). Zinc, iron, stannous chloride, etc. are used as the metal and metallic salt, while palladium carbon, platinum oxide, Raney nickel, etc. are used as the catalyst for the catalytic reduction.

(Step 3)

In this step, a compound represented by the general formula (VII) is cyclized by heating or warming in the absence of any solvent or in the presence of a commonly employed organic solvent to prepare a five-membered lactam represented by the general formula (VIII). This reaction is usually conducted in an alcohol solvent such as methanol, ethanol or butanol, an alkyl halide solvent such as dichloromethane, chloroform, dibromoethane or dichloroethane, a hydrocarbon solvent such as benzene, toluene or xylene, an ether solvent such as tetrahydrofuran or diglyme, or other solvents such as N,N-dimethylformamide or dimethyl sulfoxide.

When the reduction of the nitro group in step 2 is conducted at a high temperature, optionally in an autoclave, a cyclized compound (VIII) can be prepared without isolation of the compound (VII).

(Step 4)

In this step, a mixture of a five-membered lactam in the cis form with a five-membered lactam in the trans form each represented by the general formula (VIII) is heated in the presence or absence of a base in an organic solvent to isomerize the cis lactam, thereby obtaining only the trans lactam represented by the general formula (IX). A preferred example of the reaction methods is one wherein the reaction is conducted by heating the mixture either in ethanol or a mixed solvent comprising ethanol and xylene in the presence of potassium tert-butoxide, or in xylene in the presence of potassium trimethylsilanolate.

(Step 5)

In this step, the trans five-membered lactam represented by the general formula (IX) is reduced with diborane or a metal-hydrogen complex compound to prepare a pyrrolidine derivative represented by the general formula (X). Preferred metal-hydrogen complex compounds include aluminum lithium hydride and bis(2-methoxyethoxy)aluminum sodium hydride, and the reduction is conducted in an ether solvent such as ether, tetrahydrofuran or diglyme, or an aromatic hydrocarbon solvent such as benzene, toluene or xylene.

(Step 6)

In this step, the compound represented by the general formula (X) is treated with boron tribromide, boron trichloride, hydrobromic acid, hydriodic acid, or any other agent which causes ether linkage cleavage to remove the protective group, thereby preparing a compound represented by the general formula (XI).

<Preparation Process 2>

The cis form of the compound of the present invention can be prepared by, e.g., treating the adduct represented by the general formula (VI) and obtained in step 1 of Process 1, or the amino ester (VII) obtained in step 2 of Process 1 by silica gel column chromatography to isolate a desired isomer and then conducting the same procedure as that of Process 1 (except for step 4).

<Preparation Process 3>

The compound represented by the general formula (I) contains optically active d and l isomers besides the positional isomers of cis and trans forms. Resolution of the optical isomers is conducted by an ordinary method, and examples thereof include a method wherein the mixture is passed through a column for separating optical isomers, such as a chiral column, and a method wherein the isomers are separated in the form of a salt with an optically active acid, such as (+)-tartaric acid, (+)-camphoric acid, (+)-dibenzoyl tartrate, (+)-10-camphorsufonic acid, or (+)-mandelic acid from a suitable solvent by fractional re-crystallization. The acid may be used in the (−) form.

The optically active substance represented by the general formula (I) can be obtained by subjecting the compound represented by the general formula (X) or a derivative thereof to optical resolution in the same method as that described above and then conducting the reaction of step 6.

<Preparation Process 4>

When Y in the general formula (I) is a group represented by the formula —CH$_2$— (i.e., when n is 1), the compound of the present invention may be prepared also by the following process:

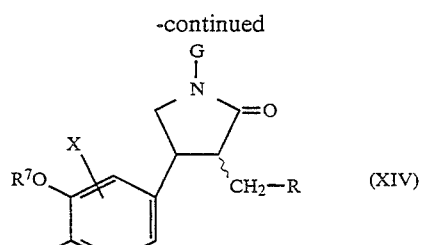

(XII)

step 7
(protection)

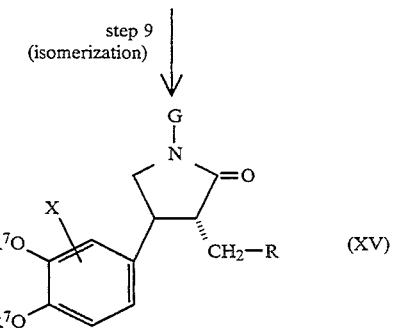

(XIII)

step 8
(alkylation)

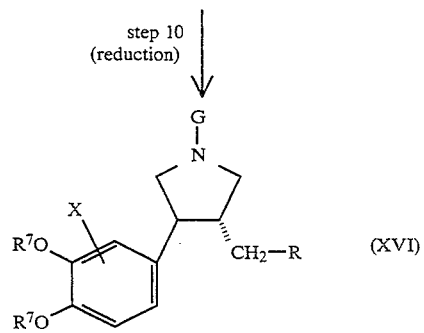

(XIV)

step 9
(isomerization)

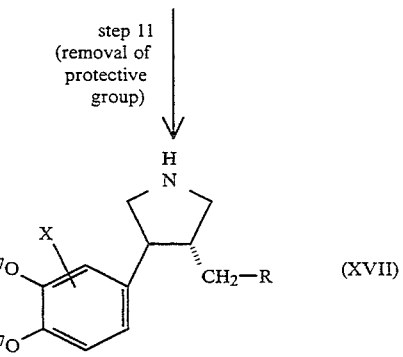

(XV)

step 10
(reduction)

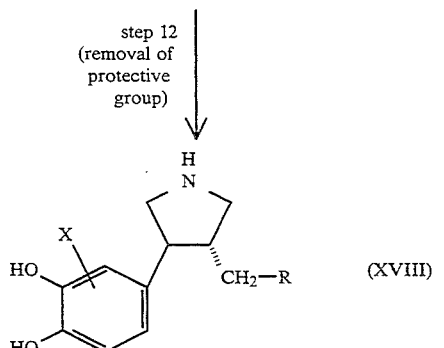

(XVI)

step 11
(removal of protective group)

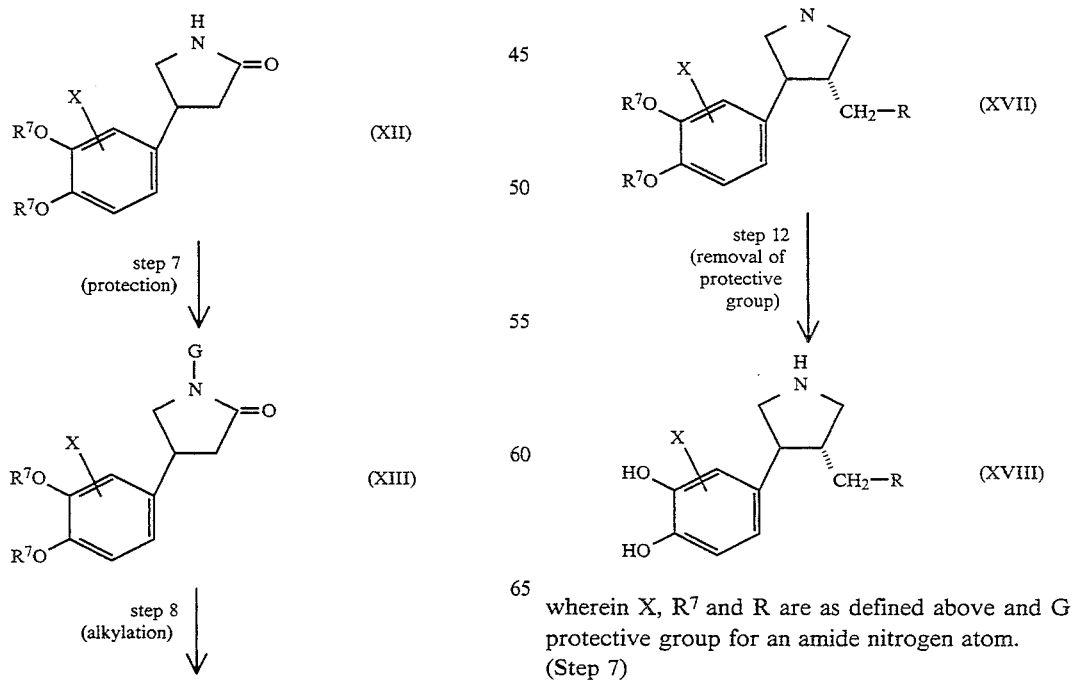

(XVII)

step 12
(removal of protective group)

(XVIII)

wherein X, R$^7$ and R are as defined above and G is a protective group for an amide nitrogen atom.
(Step 7)

In this step, the nitrogen atom of the compound represented by the general formula (XII) is protected. Examples of the protective group for the amide include substituted and unsubstituted benzyl, aryl, and alkoxyalkyl groups. Among them, benzyl, 3,4-dimethoxybenzyl, and 3-methoxymethyl groups are preferred.

This step is conducted by a customary method. A halide of the above-described substituted or unsubstituted benzyl or acyl group or the like may be preferably reacted with a compound (XII) to prepare a compound (XIII). It is preferred that the above-described reaction be conducted in the presence of a base. Examples of the base include alkylammonium hydroxide such as tetrabutylammonium hydroxide, tertiary amine, and metal hydride such sodium hydride. In this case, terahydrofuran, ether, benzene, toluene, xylene, etc. are preferably used as a solvent.

(Step 8)

In this step, a substituent is introduced into the α-position of the carbonyl group of a compound represented by the general formula (XIII).

A preferred method of introducing the substituent comprises adding a compound represented by the general formula R—CH$_2$—Z wherein Z is an eliminatable group, such as a halogen, a toluenesulfonyloxy group, or a methanesulfonyloxy group, to the compound represented by the general formula (XIII) in tetrahydrofuran in the presence of lithium diisopropylamide or sodium hydride, and causing them to react with each other.

(Step 9)

The reaction is conducted according to the method of step 4 described in detail in Process 1.

Specifically, a mixture of a five-membered ring lactam in cis form with a five-membered ring lactam in trans form represented by the general formula (XIV) is heated in the presence or absence of a base to isomerize the cis lactam, thereby obtaining only the trans lactam represented by the general formula (XV). A preferred method of conducting this step comprises heating the above-described mixture either in the presence of potassium tert-butoxide in a mixed solvent comprising ethanol and xylene, or in the presence of potassium trimethylsilanolate in xylene.

(Step 10)

The reaction is conducted according to the method of step 5 described in detail in Process 1.

Specifically, the five-membered ring lactam represented by the general formula (XV) is reduced with diborane or a metal-hydrogen complex compound to prepare a pyrrolidine derivative represented by the general formula (XVI). Preferred examples of the metal-hydrogen complex compound include lithium aluminum hydride and bis(2-methoxyethoxy)aluminum sodium hydride, and the reaction is conducted in an ether solvent such as ether, tetrahydrofuran or diglyme, or an aromatic hydrocarbon solvent such as benzene, toluene or xylene.

(Step 11)

In this step, the protective group introduced in step 7 is removed. The method of conducting this step varies depending upon the reactant used in step 7. However, when benzyl halide is used in step 7, hydrogenation is conducted in the presence of a metallic catalyst such as palladium/carbon or Raney nickel. In some cases, this step may be conducted simultaneously with step 12.

(Step 12)

The reaction is conducted according to the method of step 6 described in detail in Process 1.

Specifically, a compound represented by the general formula (XVII) is treated with boron tribromide, boron trichloride, hydrobromic acid, or any other agent which causes ether linkage cleavage to remove the protective group, thereby preparing a compound represented by the general formula (XVIII).

The compounds and their salts of the invention are useful in the pharmaceutical field. Some were tested from the pharmacological point of view. Procedures and results are described below.

Preferred Embodiments

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

1. Test on specific binding of D1 and D2 receptors in the striatum of rat

The striatum of rats were excised, homogenized with a 0.05M Tris Fuffer and then centrifuged at 20,000×g to collect its synaptosome fraction. The sediment was washed several times with a 0.25M Tris Buffer and suspended in a 0.05M Tris Buffer containing 120 mM of Nacl, 5 mM of KCl, 2 mM of CaCls and 1 mM of MgCl2. The suspension was, in portions, placed in the frozen state at minus 80 degree centigrade. $^3$H-Sch23390 having a final concentration of 0.3 nM in the case of D1 and $^3$H-Spiperone having a finish concentration of 0.2 nM in the case of D2 were added to the portions of the suspension, respectively, together with a specimen. The mixtures were incubased at 37 degree centigrade for 15 minutes. Having been filtrated with a Whatman GF/B filter, they were examined with a liquid scintillation counter. SKF-82526 and Spiperone were each used for the determination of nonspecific binding. IC$_{50}$ means a concentration of the test material which can be replaced for 50% of the binding of a radioisotope-labelled Sch23390 or Spiperone. Results are shown in Table 1. The test compounds A to L are listed below.

Test compounds:

Compound A: trans-3-(3,4-dihydroxyphenyl)-4-phenyl-pyrrolidine hydrobromide

Compound B: trans-3-(3,4-dihydroxyphenyl)-4-(2-methylphenyl)pyrrolidine hydrobromide Compound C: trans-3-(2-chlorophenyl)-4-(3,4-dihydroxyphenyl)pyrrolidine hydrobromide Compound D: trans-3-(2-chloro-3-hydroxyphenyl)-4-(3,4-dihydroxyphenyl)pyrrolidine hydrobromide Compound E: trans-3-(3,4-dihydroxyphenyl)-4-(3-methylthienyl)pyrrolidine hydrobromide Compound F: cis-3-(3,4-dihydroxyphenyl)-4-(3-methylthienyl)pyrrolidine hydrobromide Compound G: trans-3-(7-benzothiophenyl)-4-(3,4-dihydroxyphenyl)pyrrolidine hydrobromide Compound H: trans-3-(3-chloro-6-hydroxyphenyl)-methyl-4-(3,4-dihydroxyphenyl)-pyrrolidine Compound I: trans-3-(2,6-dihydroxyphenyl)methyl-4-(3,4-dihydroxyphenyl)pyrrolidine Compound J: trans-3-(3-chloro-2,6-dihydroxyphenyl)-methyl-4-(3,4-dihydroxyphenyl)-pyrrolidine
Compound K: trans-3-(3,5-difluoro-2-hydroxyphenyl)-methyl-4-(3,4-dihydroxyphenyl)-pyrrolidine
Compound L: trans-3-(3-fluoro-2-hydroxyphenyl)methyl-4-(3,4-dihydroxyphenyl)pyrrolidine

TABLE 1

| Compd. | $IC_{50}$ ($10^{-6}$M) | |
|---|---|---|
| | D1 | D2 |
| A | 4.80 | 88 |
| B | 0.60 | 10 |
| C | 0.60 | 7 |
| D | 0.38 | 5.3 |
| E | 0.17 | 90 |
| F | 9.00 | 50 |
| G | 0.40 | 6.0 |
| H | 0.3 | 0.3 |
| I | 0.2 | 0.07 |
| J | 0.13 | 1.0 |
| K | 0.13 | 2.0 |
| L | 0.2 | 5.0 |
| dopamine | 5.50 | 2.0 |

2. Action cardiohemodynamics in anesthetized dogs

Mongrel dogs of about 10 kg were anesthetized with the intravenous administration of 20 mg/kg of thiopental sodium. They were then treated by introducing oxygen gas, nitrous oxide gas and enflurane in combination through an endotracheal tube inserted thereinto to conduct artificial respiration and with an Acoma artificial respirator ARF-850E (trademark) and an Acoma anesthesia apparatus EM-A (trademark) to keep the anesthesia still effective. The aortic pressure and the internal pressure of the left ventricle were determined with a micro-tip catheter pressure transducers, MPC-500, tradename of Miller, inserted at the femoral arteries. The renal blood pressure was determined by exposing by laparotomy the renal artery to a probe of an electromagnetic blood flowmeter, MFV-2100, tradename of Nihon Kohden Corp. Results are caught with a polygraph system, RM-6000, tradename of Nihon Kohden Corp.

The specimen was dissolved in a 0.9% saline solution and administered at the brachial vein through a catheter inserted thereinto. When the administration was made at the duodenum, the duodenum was exposed by the median incision to a catheter inserted thereinto. Results are shown in terms of an increase in percent of the renal blood flow and a decrease in percent of the mean blood pressure when the test compound was administered.

| test compound | administered amount | increase of renal blood pressure (%) | decrease of mean blood pressure (%) |
|---|---|---|---|
| | intravenously | | |
| B | 10 (microgram/ 10 kg) | 13 | 23 |
| C | | 19 | 21 |
| D | 3 | 20 | 15 |
| E | 10 | 20 | 15 |
| H | 3 | 20 | 15 |
| I | 3 | 25 | 29 |
| J | 1 | 33 | 22 |
| K | 1 | 15 | 17 |
| L | 3 | 26 | 21 |
| | at duodenum | | |
| E | 1.0 | 20 | 13 |
| K | 1.0 | 16 | 11 |

3. Effect on the acute heart failure of anesthetized dogs

The dogs were treated in the same way as shown in Test 2 and their chest was exposed in the fourth intercostal space of the left theracotomy. An electro-magnetic flow probe was placed around the aorta of the origin to determine the cardiac output. The left anterior descending coronary artery (LAD) was dissected free at just distal to the first diagonal branch, and a thread was placed around it to ligate. The acute cardiac failure was prepared as follows. Five hundred ml of 0.9% saline was intravenously infused in about 2 hours, then 500 ml of 6% Dextran 70 injection of Midori Juji Co., Ltd. containing 10 mg of propranolol and 300 mg of creatinine was infused rapidly in about 30 minutes to increase left venticular end diastolic pressure (LVEDP) to about 20 mmHg. The infusion rate of the same dextran injection was decreased down to about one third to maintain the congestion. After the congestion state became stable, the LAD was ligated to worsen the congestion. The LVEDP increased to more than 25 mm Hg. At this time, the intravenous infusion of 0.3 microgram/kg/min of the hydrochloride salt of Compound D was started. The LVEDP decreased about 3 mm Hg by this infusion. Cardiac output and reval blood flow decreased about 20% and 10%, respectively, by the ligation of LAD.

The infusion of the compound D hydrochloride recovered the cardiac output by about 10% and increased the renal blood flow over the preligation level. These results suggest that the compound of the present invention is effective for heart failure.

Example 1

(±)-trans-3-(2-Chloro-3-hydroxyphenyl)-4-(3,4-dihydroxyphenyl)pyrrolidine hydrobromide

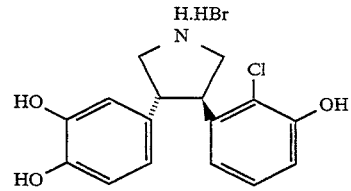

(i) 84 g of 2-chloro-3-methoxybenzaldehyde, 200 ml of nitromethane, and 38 g of ammonium acetate were refluxed in 50 ml of acetic acid for 1.5 hr. The reaction mixture was poured into 1.5 l of water, and precipitated crystals were separated by filtration and recrystallized from ethanol, thereby preparing 58 g of 2-chloro-3-methoxy-β-nitrostyrene.

m.p.: 98°–100° C.

(ii) 19.3 g (0.19 mol) of dried isopropylamine was dissolved in 100 ml of anhydrous tetrahydrofuran. The solution was cooled to −60° C. or below in a dry ice/acetone bath, and 120 ml of a solution of 1.6M n-butyllithium in n-hexane was dropwise added thereto at this temperature with stirring. The mixture was stirred for 15 min, and a solution of 40.37 g (0.18 mol) of ethyl 3,4-dimethoxyphenylacetate in 200 ml of anhydrous tetrahydrofuran was dropwise added thereto at the same temperature. After stirring for additional 15 min, a solution of 38.45 g (0.18 mol) of 2-chloro-3-methoxy-β-nitrostyrene in 400 ml of anhydrous tetrahydrofuran was dropwise added thereto with stirring at such a dropping rate that the temperature of the system did not exceed −50° C. After stirring for 30 min, a small amount of water was added thereto and tetrahydrofuran was distilled off to some extent in vacuo. A 6N hydrochloric acid solution was added to the residue for acidification, and the acidified residue was extracted twice with dichloromethane. The resultant organic phase was washed twice with a saturated saline solution and dried over anhydrous magnesium sulfate. The solvent was distilled off in vacuo, and the residue was purified by silica gel column chromatography (eluted with a n-hexane/ethyl acetate mixture in a n-hexane to ethyl acetate ratio of 2:1) to prepare 75.1 g of viscous crude ethyl 3-(2-chloro-3-methoxyphenyl)-2-(3,4-dimethoxyphenyl)-4-nitrobutyrate.

(iii) 148.9 g (0.34 mol) of the above-described nitro ester and 200 ml of concentrated hydrochloric acid were dissolved in 1000 ml of ethanol and the solution was stirred under reflux. 112.4 g (1.72 mol) of zinc dust was added thereto in portions. After stirring under reflux or 2 hr, the solid matter was removed by filtration, and the filtrate was concentrated in vacuo. Dichloromethane was added to the residue, and the mixture was made basic with a 10% aqueous sodium hydroxide solution. Then, the mixture was passed through Celite to removed precipitated solid matter by filtration and well washed with dichloromethane. The filtrate was separated into an organic phase and an aqueous phase. The aqueous phase was extracted twice with dichloromethane, and the organic phases were combined with each other. The combined organic phase was washed twice with a saturated saline solution and dried over anhydrous magnesium sulfate. The solvent was distilled off in vacuo to prepare 135 g of viscous crude ethyl 4-amino-3-(2-chloro-3-methoxyphenyl)-2-(3,4-dimethoxyphenyl)butyrate.

Part of the product was purified by silica gel column chromatography (eluted in a chloroform to methanol ratio of 98:2) and converted into a hydrochloride with hydrogen chloride in ethanol.

m.p.: 239°–241° C. (decomposed)

elementary analysis: as $C_{21}H_{26}ClNO_5 \cdot HCl$

|  | C | H | N |
|---|---|---|---|
| calculated (%): | 56.76 | 6.12 | 3.15 |
| found (%): | 56.52 | 6.08 | 3.01 |

(iv) 69.5 g (0.17 mol) of the above-described amino ester was refluxed in 500 ml of xylene for 5 hr. After the reaction mixture was cooled, xylene was distilled off in vacuo, and ether was added to the residue for solidification, thereby preparing 60.5 g of 3-(2-chloro-3-methoxyphenyl)-4-(3,4-dimethoxyphenyl)-2-pyrrolidone (a mixture of cis and trans forms).

(v) 108 g (0.3 mol) of the above-described 2-pyrrolidone derivative comprising a mixture of cis and trans forms was dissolved in 1600 ml of xylene, and 5.2 g (0.04 mol) of potassium trimethylsilinolate was added thereto in portions under reflux with stirring. After stirring under reflux for 2 hr, xylene was distilled off in vacuo, and dichloromethane was added to the residue. The mixture was washed twice with dilute hydrochloric acid and then with a saturated saline solution, and dried over anhydrous magnesium sulfate. The solvent was distilled off, and the residue was recrystallized from ethanol to prepare 63.5 g of trans-3-(2-chloro-3-methoxyphenyl)-4-(3,4-dimethoxyphenyl)-2-pyrrolidone.

m.p.: 149°–151° C.

NMR(400 MHz in CD$_3$OD) δ; 3.45(1H, dd, J=10 Hz, 10 Hz), 3.82(3H, s), 3.83(3H, s), 3.86(1H, dd, J=8 Hz; 10 Hz), 3.89(3H, s), 3.94(1H, d, J=10 Hz), 4.32 (1H, ddd, J=8 Hz, 10 Hz, 10 Hz), 6.78(1H, dd, J=2 Hz, 8 Hz), 6.84(1H, d, J=2 Hz), 6.90 (1H, d, J=2 Hz), 6.90(1H, d, J=8 Hz), 7. 01 (1H, dd, J=1 Hz, 8 Hz), 7.22(1H, dd, J=1 Hz, 8 Hz), 7.34(1H, dd, J=8 Hz, 8 Hz)

Nuclear Overhauser effects (NOE) of 3 and 5% were observed between hydrogen (δ: 4.32) at the 4-position of the 2-pyrrolidone ring and hydrogens (δ: 6.78, 6.84) on the 3,4-dimethoxyphenyl ring.

(vi) 18.5 g (0.051 mol) of the above-described trans-2-pyrrolidone derivative was dissolved in 700 ml of hot tetrahydrofuran, and the solution was dropwise added to 180 ml of a 1M borane/tetrahydrofuran solution while passing a stream of nitrogen thereinto with cooling in an iced water bath. Subsequently, the mixture was stirred under reflux for 5 hr and then allowed to stand for cooling. To the reaction mixture, 50 ml of a 6N hydrochloric acid solution was gradually added thereto, and the mixture was stirred under reflux for 1 hr to decompose an amine-borane complex. After cooling the mixture, tetrahydrofuran was distilled off in vacuo and a 10% sodium hydroxide solution was added to the residue for alkalinization. The alkalinized residue was extracted three time with dichloromethane. The dichloromethane solution was washed twice with a saturated saline solution and then dried over anhydrous magnesium sulfate. Dichloromethane was distilled off, and the residue was purified by medium-pressure silica gel column chromatography (eluted first with a chloroform/methanol mixture in a chloroform to methanol ratio of 95:5 and then with methanol only) to prepare 11 g of viscous trans-3-(2-chloro-3-methoxyphenyl)-4-(3,4-dimethoxyphenyl)pyrrolidine.

(vii) 2.6 g of the above-described transpyrrolidine derivative was dissolved in dried dichloromethane and cooled with iced water, and 33.7 ml of 1M boron tribromide in dichloromethane was dropwise added thereto while stirring in a stream of nitrogen. After the completion of the dropwise addition, the temperature of the mixture was returned to room temperature, and the mixture was then stirred for 5 hr. The reaction mixture was cooled to −20° C., and 10 ml of methanol was added thereto. The solution was distilled off in vacuo, and methanol was added to the residue. The resulting solution was again distilled in vacuo. This procedure was repeated three times, and the residue was recrystallized from ethanol/acetonitrile to prepare 1.36 g of trans-3-(2-chloro-3-hydroxyphenyl)-4-(3,4-dihydroxyphenyl)-pyrrolidine hydrobromide.

m.p.: 218°–219° C.

NMR(400 MHz in D$_2$O) δ; 3.45(1H, t, J=11 Hz), 3.56(1H, t, J=11 Hz), 3.80~3.89(1H, m), 4.00(1H, dd, J=11 Hz, 11 Hz), 4.10(1H, dd, J=11 Hz, 11 Hz), 4.31 (1H, ddd, J=11 Hz, 11 Hz; 8 Hz), 6.85(1H, dd, J=8 Hz, 2 Hz), 6.91(1H, d, J=8 Hz), 6.96 (1H, d, J=2 Hz), 7.04(1H, dd, J=8 Hz, 2 Hz), 7.18(1H, d, J=8 Hz), 7.32(1H, d, J=8 Hz)

elementary analysis: as $C_{16}H_{17}ClNO_3 \cdot HBr \cdot 0.3H_2O$

|  | C | H | N |
|---|---|---|---|
| calculated (%): | 49.00 | 4.38 | 3.57 |
| found (%): | 49.04 | 4.30 | 3.43 |

Example 2

(±)-trans-3-(3,4-Dihydroxyphenyl)-4-(3-methylthienyl)pyrrolidine hydrobromide

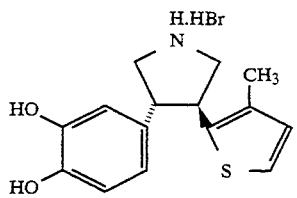

(i) 6.31 g (0.05 mol) of 3-methylthienylcarboxaldehyde was dissolved in 40 ml of acetic acid, and 13 ml of nitromethane and 3.85 g of ammonium acetate were added thereto. The mixture was stirred under reflux for 2.5 hr. After cooling, the reaction mixture was concentrated in vacuo, and 70 ml of 70% ethanol was added thereto. The formed crystal was recovered by filtration to prepare 3-methyl-2-(2-nitrovinyl)thiophene.

m.p.: 65°-67° C.

(ii) 2.44 ml of diisopropylamine was dissolved in 15 ml of anhydrous tetrahydrofuran, and the solution was cooled to −60° C. or below in a dry ice/acetone bath. 9.88 ml of a solution of 1.6M n-butyllithium in n-hexane was dropwise added thereto with stirring. After the completion of the dropwise addition, the mixture was stirred for 15 min, and a solution of 3.54 g (0.0158 mol) of ethyl 3,4-dimethoxyphenylacetate in 7 ml of anhydrous tetrahydrofuran was dropwise added thereto at the same temperature. After the completion of the dropwise addition, the mixture was stirred for additional 15 min, and a solution of 2.86 g (0.0158 mol) of 3-methyl-2-(2-nitrovinylene)thiophene in 16 ml of anhydrous tetrahydrofuran was dropwise added thereto at the same temperature. After the completion of the dropwise addition, the mixture was stirred for 30 min, and 0.5 ml of water was added thereto. Then, the solvent was distilled off in vacuo. The residue was dissolved in 100 ml of dichloromethane, and the solution was washed with a 3N hydrochloric acid solution and then with a saturated saline solution. The resultant dichloromethane phase was dried over anhydrous magnesium sulfate. The solvent was distilled off in vacuo to prepare crude ethyl 2-(3,4-dimethoxyphenyl)-3-(3-methylthienyl)-4-nitrobutyrate.

(iii) 3.68 g (9.35 mmol) of the above-described nitro ester was dissolved in 17 ml of ethanol, and 5.61 ml of concentrated hydrochloric acid and 0.61 g of powdery zinc were added thereto. The mixture was heated under reflux for 24 hr. After cooling the mixture, solid matter was removed by filtration, and the filtrate was concentrated in vacuo. Dichloromethane was added to the residue, and the mixture was alkalinized with a 2N aqueous sodium hydroxide solution. Then, the mixture was passed through Celite to remove precipitated solid matter by filtration. The organic phase of the filtrate was separated. The aqueous phase was extracted twice with dichloromethane, and the organic phases were combined with each other. The combined organic phase was washed twice with a saturated saline solution and dried over anhydrous magnesium sulfate. Then, the solvent was distilled off in vacuo, and the residue was separated and purified by medium-pressure silica gel column chromatography (dichloromethane:methanol=95:5) to prepare 1.2 g of 3-(3,4-dimethoxyphenyl)-4-(3-methylthienyl)-2-pyrrolidone and 1.6 g of ethyl 4-amino-2-(3,4-dimethoxyphenyl)-3-(3-methylthienyl)-butyrate.

(iv) 1.1 g of the above-described 2-pyrrolidone derivative was dissolved in 20 ml of ethanol. 50 mg of potassium tert-butoxide was added to the solution, and the mixture was heated under reflux for 2 hr. After cooling the mixture, the solvent was distilled off, and 50 ml of dichloromethane was added to the residue for dissolution. The solution was washed with a 2N hydrochloric acid and then with a saturated saline solution. The organic phase was dried over anhydrous magnesium sulfate. Dichloromethane was distilled off in vacuo, and the residue was recrystallized from ethanol to prepare 0.9 g of trans-3-(3,4-dimethoxyphenyl)-4-(3-methylphenyl)-2-pyrrolidone.

m.p.: 138°-140° C.

(v) A solution of 1.81 g (5.7 mmol) of the above-described trans-2-pyrrolidone derivative in 100 ml of tetrahydrofuran was dropwise added to 22.8 ml of 1M borane/tetrahydrofuran in a cooled state in a stream of nitrogen. The mixture was stirred for 15 min and heated under reflux for 10 hr. After cooling the reaction mixture, 5 ml of a 6N hydrochloric acid was added thereto, and the mixture was heated at 60° C. for 30 min. After cooling, the reaction mixture was concentrated in vacuo and a 2N aqueous sodium hydroxide solution was added to the residue. The mixture was extracted with dichloromethane, and the extract was washed with a saturated saline solution and dried over anhydrous magnesium sulfate. The solvent was distilled off in vacuo, and the residue was purified by medium-pressure silica gel column chromatography (eluted first with a chloroform-methanol mixture in a chloroform to methanol ratio of 95:5 and then with methanol only) to prepare 0.96 g of oleaginous trans-3-(3,4-dimethoxyphenyl)-4-(3-methylthienyl)pyrrolidine.

(vi) 1.32 g (4.35 mmol) of the above-described trans-pyrrolidine derivative was dissolved in 5 ml of dichloromethane, and 13.1 ml of a solution of 1M boron tribromide in dichloromethane was added to the solution while cooling with ice. After the completion of the dropwise addition, the mixture was stirred at room temperature for 3 hr, and 3 ml of methanol was added thereto at −20° C. The reaction mixture was concentrated in vacuo and methanol was added again. The mixture was concentrated, and the residue was recrystallized from ethanol to prepare 1.4 g of trans-3-(3,4-dihydroxyphenyl)-4-(3-methylthienyl)-pyrrolidine hydrobromide.

m.p.: 271°-272 ° C. (decomposed)

NMR(400 MHz in CD$_3$OD) δ; 1.89(3H, s), 3.26~3.32(1H, m), 3.37( 1H, dd, J=7 Hz; 9 Hz), 3.44(1H, t, J=11 Hz), 3.79(1H, dd, J=7 Hz, 11 Hz), 3.83~3.92 (2H, m), 6.56(1H, dd, J=2 Hz, 8 Hz), 6.64 (1H, d, J=2 Hz), 6.72(1H, d, J=5 Hz), 7.19 (1H, d, J=5 Hz)

elementary analysis: as C$_{15}$H$_{17}$NO$_2$S.HBr

|  | C | H | N |
| --- | --- | --- | --- |
| calculated (%): | 50.57 | 5.09 | 3.93 |
| found (%): | 50.37 | 4.99 | 3.96 |

Example 3

(±)-trans-3-(3,4-Dihydroxyphenyl)-4-(3-methoxyphenyl)pyrrolidine hydrochloride

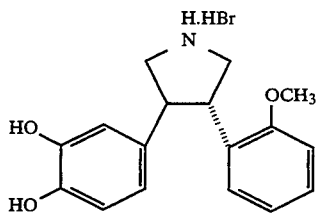

(i) Lithium diisopropylamide was prepared at −70° C. in tetrahydrofuran in a stream of nitrogen from 5.2 ml (37 mmol) of diisopropylamine and 23 ml (37 mmol) of a solution of 1.6M n-butyllithium in 23 ml (37 mmol) of n-hexane, and a solution of 6.8 g (35 mmol) of ethyl o-methoxyphenylacetate in 20 ml of tetrahydrofuran was dropwise added thereto at −70° C. After 15 min, 6.76 g (35 mmol) of 3,4-methylenedioxy-β-nitrostyrene dissolved in 200 ml of tetrahydrofuran was dropwise added thereto at the same temperature. After stirring for 30 min, a small amount of water was added to the mixture, and the reaction mixture was concentrated in vacuo. Then, a 3N hydrochloric acid solution was added to the residue for acidification, and the acidified residue was extracted with dichloromethane. The extract was washed with a saturated saline solution and dried over anhydrous magnesium sulfate, and dichloromethane was distilled off. The residue was purified by silica gel column chromatography (eluted with a n-hexane/ethyl acetate mixture in a n-hexane to ethyl acetate ratio of 3:1) to prepare 12.13 g of ethyl 2-(2-methoxyphenyl)-3-(3,4-methylenedioxyphenyl)-4-nitrobutyrate.

(ii) 8.36 g (21.6 mmol) of the above-described nitro ester derivative was dissolved in 45 ml of ethanol. 12.6 ml of concentrated hydrochloric acid and 4.2 g of powdery zinc were added to the solution, and the mixture was heated under reflux for 5.5 hr. After cooling the mixture, solid matter was filtrated off and the mother liquor was concentrated in vacuo. Dichloromethane was added to the residue and the resulting solution was alkalinized with a 10% aqueous sodium hydroxide solution and passed through Celite to remove the precipitated solid matter. The dichloromethane phase was separated and washed with a saturated saline solution. The washed dichloromethane phase was dried over anhydrous magnesium sulfate, and the solvent was distilled off. The residue was purified by medium-pressure silica gel column chromatography (eluted with a chloroform/methanol mixture in a chloroform to methanol ratio of 97:3) to prepare 2.9 g of oleaginous ethyl 4-amino-2-(2-methoxyphenyl)-3-(3,4-methylenedioxyphenyl)butyrate.

(iii) 2.79 g (7.8 mmol) of the above-described amino ester was heated in 15 ml of xylene overnight under reflux. After cooling the mixture, the solvent was distilled off, and the residue was dissolved in 30 ml of ethanol. 0.1 g of potassium tert-butoxide was added to the solution, and the mixture was heated under reflux for 1.5 hr. The solvent was distilled off in vacuo, and a small amount of ethanol was added to the residue for solidification, thereby preparing 1.12 g of trans-3-(2-methoxyphenyl)-4-(3,4-methylenedioxyphenyl)-2-pyrrolidone.

(iv) 1.1 g (3.53 mmol) of the above-described trans-2-pyrrolidone derivative was dissolved in 70 ml of tetrahydrofuran. The solution was cooled and then dropwise added to 11 ml of a solution of 1M borane in tetrahydrofuran in a stream of nitrogen. The mixture was heated overnight under reflux. The reaction mixture was cooled, and 5 ml of a 6N hydrochloric acid solution was dropwise added thereto. The mixture was heated under reflux for 1.5 hr, and tetrahydrofuran was distilled off. Dichloromethane was added to the residue and the mixture was alkalinized with a 10% aqueous sodium hydroxide solution. The resultant organic phase was separated, washed with a saturated saline solution, and dried over anhydrous magnesium sulfate. The solvent was distilled off in vacuo, and the residue was purified by medium-pressure silica gel column chromatography (eluted first with a chloroform/methanol mixture in a chloroform to methanol ratio of 96:4 and then with methanol only) to prepare 360 mg of 3-(2-methoxyphenyl)-4-(3,4-methylenedioxyphenyl)pyrrolidine.

(v) 350 mg (1.18 mmol) of the above-described pyrrolidine derivative was dissolved in 15 ml of dichloromethane, and 4.7 ml of a solution of 1M boron trichloride in dichloromethane was dropwise added to the solution in a cooled state with stirring. After the completion of the dropwise addition, the mixture was stirred at room temperature for 2 hr, and methanol was added thereto at −20° C. The solvent was distilled off in vacuo. Methanol was again added to the residue and distilled off in vacuo. This procedure was repeated several times, and the residue was crystallized from acetone to prepare 250 mg of trans-3-(3,4-dihydroxyphenyl)-4-(3-methoxyphenyl)-pyrrolidine hydrochloride.

m.p.: 212°–213° C.

NMR(400 MHz in D$_2$O) δ; 3.52(1H, t, J=11 Hz), 3.63(1H, t, J=11 Hz), 3.83~4.04(4H, m), 3.89 (3H, s), 6.83 (1H, dd, J=8 Hz, 2 Hz), 6.92(1H, d, J=8 Hz), 6.93(1H, d, J=2 Hz), 7.09(1H, t, J=8 Hz), 7.16(1H, d, J=8 Hz), 7.39(1H, d, J=8 Hz), 7.43(1H, t, J=8 Hz)

elementary analysis: as $C_{17}H_{19}NO_3 \cdot HCl$

|  | C | H | N |
| --- | --- | --- | --- |
| calculated (%): | 61.72 | 6.41 | 4.23 |
| found (%): | 61.84 | 6.23 | 4.14 |

Example 4

(−)-trans-3-(2-Chloro-3-hydroxyphenyl)-4-(3,4-dihydroxyphenyl)pyrrolidine hydrobromide and hydrochloride (i) 27.6 g of trans-3-(2-chloro-3-methoxyphenyl)-4-(3,4-dimethoxyphenyl)pyrrolidine prepared in step (vi) of Example 1 was dissolved in 210 ml of chloroform, and 10 g of triethylamine was added to the solution. Then a solution of 8.8 g of acetyl chloride in 17 ml of chloroform was dropwise added thereto. The mixture was stirred overnight at room temperature, washed with a 2N hydrochloric acid solution and then with an aqueous sodium bicarbonate solution, and dried over anhydrous magnesium sulfate. The solvent was distilled off in vacuo, and the resultant residue was purified by medium pressure silica gel column chromatography (chloroform:methanol=99:1) to prepare 24.6 g of amorphous trans-1-acetyl-3-(2-chloro-3-methoxyphenyl)-4-(3,4-dimethoxyphenyl)pyrrolidine.

(ii) 4 g of the above-described acetylpyrrolidine was loaded on a column for separating optical isomers (Chiralcel OD; a product of Daicel Chemical Industries, Ltd.) and separated and purified by making use of a mixed solvent comprising n-hexane, isopropyl alcohol and diethylamine (5:2:0.005) as an element. 1.38 g of the (−) isomer having an $[\alpha]_D27$ value of −38.6° (C=1.0 in MeOH) was obtained from an early eluted fraction, and the (+) isomer having an $[\alpha]_D^{26}$ value of 36.7° (C=1.1 in MeOH) was obtained from a later eluted fraction.

(iii) 1.38 g of the above-described (−) isomer was heated in a 47% hydrobromic acid solution for 22 hr. After cooling the mixture, hydrobromic acid was distilled off in vacuo. Methanol was added to the residue and distilled off in vacuo. This procedure was repeated several times, and the residue was recrystallized from acetonitrile to prepare 0.82 g of (−)-trans-3-(2-chloro-3-hydroxyphenyl)-4-(3,4-dihydroxyphenyl)pyrrolidine hydrobromide.
m.p.: 217°–219° C.
$[\alpha]_D^{28}$: −55.0° (C=1.01 in MeOH)
elementary analysis: as $C_{16}H_{17}ClNO_3 \cdot HBr$

|  | C | H | N |
|---|---|---|---|
| calculated (%): | 49.69 | 4.44 | 3.62 |
| found (%): | 49.74 | 4.43 | 3.49 |

(iv) The above-described hydrochloride was dissolved in water, and the solution was passed through an ion exchange resin comprising DEAE Toyopearl 650 S (a product of Tosoh Corporation) to prepare a hydrochloride.
m.p.: 262° C.
$[\alpha]_D26$: −62.8° (C=1.00 in MeOH)
NMR(400 MHz in $D_2O$) δ; 3.39(1H, t, J=11 Hz), 3.52(1H, t, J=11 Hz), 3.80(1H, ddd, J=11 Hz, 11 Hz, 8 Hz), 3.98 (1H, dd, J=11 Hz, 11 Hz), 4.07(1H, dd, J=11 Hz, 11 Hz), 4.26(1H, ddd, J=11 Hz, 11 Hz, 8 Hz), 6.79(1H, dd, J=8 Hz, 2 Hz), 6.86(1H, d, J=8 Hz), 6.95~6.98(2H, m), 7.09(1H, d, J=8 Hz), 7.22(1H, t, J=8 Hz)
elementary analysis: as $C_{16}H_{17}ClNO_3S \cdot HCl$

|  | C | H | N |
|---|---|---|---|
| calculated (%): | 56.15 | 5.02 | 4.09 |
| found (%): | 56.05 | 5.02 | 4.09 |

Example 5

The (+) isomer prepared in step (ii) of Example 3 was treated in the same manner as that of step (iii) to prepare (+)-trans-3-(2-chloro-3-hydroxyphenyl)-4-(3,4-dihydroxyphenyl)pyrrolidine hydrobromide.
m.p.: 218°–220° C.
$[\alpha]_D26$: 50.0° (C=0.96 in MeOH)
Compounds prepared according to the methods described in the Examples 1 to 5 are listed respectively as Examples 6 to 40 in Tables 2 to 4.

TABLE 2

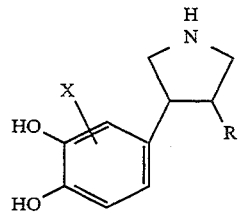

| Ex. No. | cis/ trans | X | R | m.p. (°C.) | molecular forumula | elem. anal. upper row: calcd. lower row: found C % H % N % | NMR |
|---|---|---|---|---|---|---|---|
| 6 | trans | H | Cl (phenyl) | 276~277 (dec.) | $C_{16}H_{16}ClNO_2 \cdot HBr$ | 51.85 4.62 3.78 <br> 51.73 4.69 3.49 | (400MHz in $D_2O$) δ 3.48(1H, t, J=11Hz), 3.57(1H, t, J=11Hz), 3.87(1H, ddd, J=11Hz, 11Hz, 8Hz), 4.01 (1H, dd, J=11Hz, 11Hz, 1H), 4.11 (1H, dd, J=11Hz, 11Hz, 1H), 4.31(1H, ddd, J=11Hz, 11Hz, 8Hz), 6.85(1H, dd, J=8Hz, 2Hz), 6.91(1H, d, J=8Hz), 7.36 (1H, dt, J= 8Hz, 2Hz), 7.45(1H, t, J= 8Hz), 7.49(1H, d, J=8Hz), 7.62 (1H, dd, J=8Hz, 2Hz) |
| 7 | trans | H | $CF_3$ (phenyl) | 262~263 (dec.) | $C_{17}H_{16}F_3NO_2 \cdot HB4$ | 50.51 4.24 3.47 <br> 50.17 4.14 3.17 | (400MHz in $D_2O$) δ 3.48(1H, t, J=11Hz), 3.64(1H, t, J=11Hz), 3.96~4.11(4H, m), 6.83 (1H, d, J=8z), 6.88(1H, d, J=8Hz), 6.94(1H, d, J=2Hz), 7.54(1H, t, 8Hz), 7.76~7.83(2H, m), 7.93(1H, d, J=8Hz) |

TABLE 2-continued

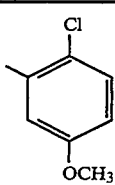

| Ex. No. | cis/ trans | X | R | m.p. (°C.) | molecular formula | elem. anal. upper row: calcd. lower row: found C % | H % | N % | NMR |
|---|---|---|---|---|---|---|---|---|---|
| 8 | trans | H | 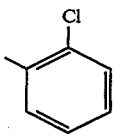 | 248~250 (dec.) | C₁₇H₁₈ClNO₃·HCl | 57.32<br>57.01 | 5.37<br>5.38 | 3.93<br>3.65 | (400MHz in D₂O) δ 3.47(1H, t, J=11Hz), 3.56 (1H, t, J=11Hz), 3.81~ 3.89(4H, m), 3.89(3H, m), 4.01 (1H, dd, J=11Hz, 11Hz), 4.10 (1H, dd, J=11Hz, 11Hz), 4.25 (1H, ddd, J=11Hz, 11Hz, 8Hz), 6.86~6.94(3H, m), 6.98(1H, d, J=2Hz), 7.16(1H, d, J=2Hz), 7.37(1H, d, J=9Hz) |
| 9 | trans | 2-Cl | 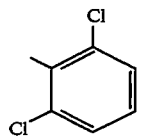 | 248~250 (dec.) | C₁₆H₁₅Cl₂NO₂·HBr | 47.44<br>47.45 | 3.98<br>3.95 | 3.46<br>3.46 | (400MHz in D₂O) δ 3.46(1H, t, J=11Hz), 3.51(1H, t, J=11Hz), 4.12(1H, t, J=11Hz), 4.14(1H, t, J=11Hz), 4.36~4.50 (2H, m), 6.91(1H, d, J=8Hz), 7.01(1H, d, J=8Hz), 7.31~7.40 (2H, m), 7.49(1H, dd, J=8Hz, 2Hz), 7.57(1H, dd, J=8Hz, 2Hz) |
| 10 | trans | H | 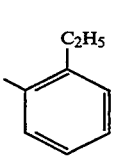 | >300 | C₁₆H₁₅Cl₂NO₂·HBr·½H₂O | 46.41<br>46.26 | 4.14<br>4.08 | 3.38<br>3.14 | (400MHz in D₂O) δ 3.63(1H, t, J=11Hz), 3.90~ 3.98(2, m), 4.17(1H, t, J=11Hz), 4.37(1H, ddd, J=11Hz, 11Hz, 8Hz), 4.71(1H, t, J=11Hz), 6.80(1H, d, J=8Hz), 6.88(1H, d, J=8Hz), 6.94(1H, s), 7.30(1H, t, J=8Hz), 7.46(2H, m) |
| 11 | trans | H | 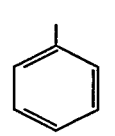 | 225~226 | C₁₈H₂₁NO₂·HBr | 59.35<br>59.26 | 6.09<br>6.14 | 3.85<br>3.64 | (400MHz in D₂O) δ 1.03(1H, t, J=7Hz), 2.60(1H, dd, J=7Hz, 3Hz,), 3.49(1H, t, J=14Hz), 3.66(1H, t, J=11Hz), 3.84(1H, ddd, J=11Hz, 11Hz, 8Hz), 3.97~ 4.05(3H, m), 6.81(1H, dd, J= 8Hz, 2Hz), 6.91(1H, d, J=8Hz), 6.91(1H, d, J=2Hz), 7.33(1H, dd, J=8Hz, 2Hz), 7.37(1H, dt, J=8Hz, 2Hz), 7.44(1H, dt, J=8Hz, 2Hz), 7.66(1H, d, J=8Hz) |
| 12 | trans | H | 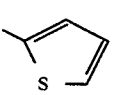 | 242~244 (dec.) | C₁₆H₁₇NO₂·HBr | 57.16<br>56.90 | 5.40<br>5.42 | 4.17<br>4.08 | (400MHz in D₂O) δ 3.54(1H, t, J=11Hz), 3.60(1H, t, J=11Hz), 3.70~ 3.78(2H, m), 4.00(1H, dd, J=7Hz, 12Hz), 4.04(1H, dd, J=7Hz, 12Hz), 6.83(1H, dd, J=2Hz, 8Hz), 6.92(1H, d, J=2Hz), 6.94(1H, d, J=4Hz), 7.40~7.50(5H, m) |
| 13 | trans | 2-Cl | (thiophene) | 212~215 (dec.) | C₁₄H₁₄NO₂SCl·HBr·H₂O | 42.60<br>42.92 | 4.34<br>4.01 | 3.55<br>3.71 | (400MHz in CD₃OD) δ 3.28(1H, t, J=11Hz), 1.49(1H, t, J=11Hz), 3.91~4.00(2H, m), 4.04~4.19(2H, m), 6.79 (1H, d, J=9Hz), 6.86 (2H, m), 7.30(1H, m) |

TABLE 2-continued

[Structure: pyrrolidine N-H connected to a ring bearing R, attached to a phenyl ring with X, and two OH groups (catechol)]

| Ex. No. | cis/ trans | X | R | m.p. (°C.) | upper row: calcd. molecular forumula | elem. anal. lower row: found C % | H % | N % | NMR |
|---|---|---|---|---|---|---|---|---|---|
| 14 | cis | H | 2-methylthiophen-3-yl (CH₃, S) | 255~256 (dec.) | C₁₅H₁₇NO₂S.HBr | 50.57 / 50.71 | 5.09 / 5.11 | 3.93 / 3.93 | (400MHz in CD₃OD) δ 1.94(3H, s), 3.59(1H, dd, J=7Hz, 12Hz), 3.64~3.80(3H, m), 3.86(1H, dd, J=7Hz, 12Hz), 4.24(1H, dd, J=7Hz, 12Hz), 6.31(1H, dd, J= 2Hz, 8Hz), 6.35(1H, d, J=2Hz), 6.62(1H, d, J=8Hz), 6.75(1H, d, J= 5Hz), 7.14(1H, d, J=5Hz) |
| 15 | trans | H | 3,4-dihydroxyphenyl | 208~210 (dec.) | C₁₆H₁₇NO₄.HBr | 52.19 / 52.20 | 4.93 / 5.17 | 3.80 / 3.26 | (400MHz in CD₃OD) δ 3.50(1H, t, J=11Hz), 3.58~ 3.62(2H, ), 3.96(1H, dd, J=7Hz, 11Hz), 6.82(1H, dd, J=2Hz, 8Hz), 6.91(1H, d, J=2Hz), 6.93(1H, d, J=8Hz) |
| 16 | trans | H | thiophen-2-yl | 238~240 (dec.) | C₁₄H₁₅NO₂S.HBr (0.3H₂O) | 48.37 / 48.37 | 4.81 / 4.69 | 4.03 / 3.94 | (400MHz in CD₃OD) δ 3.46~3.64(3H, m), 3.94(1H, dd, J=8Hz, 12Hz), 4.00~ 4.07(2H, m), 6.85(1H, dd, J= 8Hz, 12Hz), 6.92~6.94(2H, m), 7.02·8 7.05(2H, ), 7.38 (1H, dd, J=1Hz, 5H z) |
| 17 | trans | H | thiophen-3-yl | 247~248 (dec.) | C₁₄H₁₅NO₂S.HBr (0.2H₂O) | 48.62 / 48.64 | 4.78 / 4.77 | 4.05 / 3.96 | (400MHz in CD₃OD) δ 3.43~3.63(3H, m), 3.80~4.00 (3H, m), 6.82(1H, dd, J=2Hz, 8Hz), 6.91(1H, d, J=2Hz), 6.92 (1H, d, J=8Hz), 7.10(1H, dd, J=1Hz, 5Hz), 7.27(1H, dd, J=1Hz, 3Hz), 7.48(1H, dd, J= 3Hz, 5Hz) |
| 18 | trans | H | 3-methylthiophen-2-yl (CH₃, S) | 275~277 (dec.) | C₁₅H₁₇NO₂S.HCl.½H₂O | 56.16 / 55.92 | 5.96 / 5.65 | 4.36 / 4.29 | (400MHz in D₂O) δ 2.19(3H, a), 3.50~3.60(3H, m), 3.70~3.85(1H, m), 3.90~ 4.00(2H, m), 6.80(1H, dd, J=2Hz, 8Hz), 6.94(1H, d, J=8Hz), 7.23(1H, d, J=5Hz), 7.34(1H, d, J=5Hz) |
| 19 | trans | H | 2-bromophenyl | 288~289 (dec.) | C₁₆H₁₆BrNO₂.HBr | 46.27 / 46.23 | 4.13 / 4.04 | 3.37 / 3.31 | (90MHz in CD₃OD) δ 3.1~4.6(6H, m), 6.5~6.7(3H, m), 6.96~6.56(4H, m) |
| 20 | trans | H | naphthalen-1-yl | 261~263 (dec.) | C₂₀H₁₃NO₂.HBr | 62.36 / 61.76 | 5.23 / 5.19 | 3.63 / 3.51 | (90MHz in CD₃OD) δ 3.1~4.2(5H, m), 4.32~4.76 (1H, m), 6.6(2H, d), 6.7(1H, d), 7.3~7.88(6H, m), 7.9~8.1(1H, m) |
| 21 | trans | 2-CH₃ | 2-methylphenyl (CH₃) | 283~ (dec.) | C₁₈H₂₁NO₂.HBr | 59.32 / 58.97 | 6.10 / 6.00 | 3.84 / 3.77 | (90MHz in CD₃OD) δ 1.92(3H, s), 2.08(3H, s), 3.4~ 4.1(6H, m), 6.6(1H, d, J=9Hz), 6.78(1H, d, J=9Hz), 6.92~ 7.3(3H, m), 7.3~7.5(1H, m) |

TABLE 2-continued

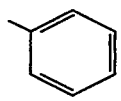

| Ex. No. | cis/ trans | X | R | m.p. (°C.) | upper row: calcd. molecular forumula | elem. anal. lower row: found C % | H % | N % | NMR |
|---|---|---|---|---|---|---|---|---|---|
| 22 | trans | 5-Cl | 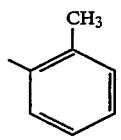 | 258~250 (dec.) | C₁₆H₁₆ClNO₂.HBr | 51.85 51.89 | 4.62 4.61 | 3.78 3.83 | (90MHz in CD₃OD) δ 3.56~3.94(6H, m), 6.54(1H, d, J=2Hz), 6.66(1H, d, J=2Hz), 7.24(5H, b, s) |
| 23 | trans | H | 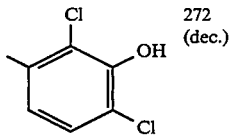 | 280~283 (dec.) | C₁₇H₁₉NO₂.HBr | 58.30 57.87 | 5.76 5.63 | 4.00 4.01 | (90MHz in CD₃OD) δ 2.18(3H, s), 3.1~4.0(6H, m), 6.4~6.7(3H, m), 6.8~7.5(4H, m) |
| 24 | trans | H | 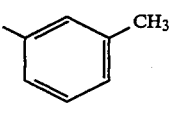 | 272 (dec.) | C₁₆H₁₅NCl₂O₃.HBr | 45.61 45.31 | 3.84 3.79 | 3.33 3.37 | (90MHz in CD₃OD) δ 1.92(3H, s), 2.08(3H, s), 3.4~4.1(6H, m), 6.6(1H, d, J=9Hz), 6.78(1H, d, J=9Hz), 6.92~7.3(3H, m), 7.3~7.5(1H, m) |
| 25 | trans | H | 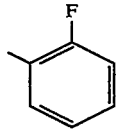 | 212~213 (dec.) | C₁₇H₁₉NO₂.HBr | 58.27 58.16 | 5.76 5.70 | 4.00 3.89 | (90MHz in CD₃OD) δ 2.24(3H, s), 3.36~3.9(6H, m), 6.5~6.7(3H, m), 6.9~7.1(4H, m) |
| 26 | trans | H | 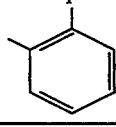 | 230~231 (dec.) | C₁₆H₁₆FNO₂.HBr | 54.23 54.10 | 4.85 4.91 | 3.95 3.83 | (90MHz in CD₃OD) δ 3.4~5(6H, m), 6.5~6.72(3H, m), 6.9~7.5(4H, m) |
| 27 | trans | 2-F | 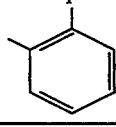 | 275~277 (dec.) | C₁₆H₁₅F₂NO₂.HBr | 51.61 51.35 | 4.34 4.10 | 3.76 3.60 | (90MHz in CD₃OD ) δ 3.26~3.14(2H, m), 3.64~4.1(4H, m), 6.4~6.66(2H, q), 6.84~7.4(4H, m) |

TABLE 3

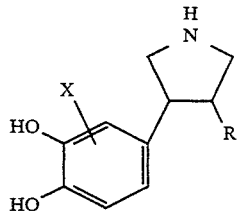

| Ex. No. | cis/trans | X | R | m.p. (°C.) | NMR |
|---|---|---|---|---|---|
| 28 | trans | H | 3-OCH₃-phenyl | 192~193 | (400MHz in D₂O) δ 3.15~3.75(4H, m), 3.87(3H, s), 3.95~4.05 (2H, m), 6.83(1H, d, J=8Hz), 6.94(1H, d, J=8Hz), 6.95(1H, d, J=3Hz), 6.99~7.05 (3H, m), 7.41(1H, t, J=8Hz) |
| 29 | trans | H | 3-Cl-4-OH-phenyl | 254~255 (dec.) | (400MHz in D₂O) δ 3.46(1H, t, J=11Hz), 3.56(1H, t, J=11Hz), 3.81(1H, ddd, J=11Hz, 11Hz, 8Hz), 4.00(1H, dd, J=8Hz, 2Hz), 6.93 (1H, d, J=8Hz), 6.98 (1H, d, J=2Hz), 7.09 (1H, d, J=2Hz), 7.33 (1H, d, J=8Hz) |

TABLE 4

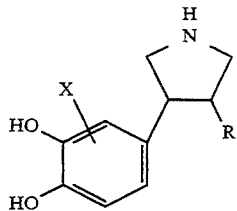

| Ex. No. | cis/trans | X | R | NMR |
|---|---|---|---|---|
| 30 | trans | H | 3-OH-phenyl | (400MHz in D₂O) δ 3.52~3.70(4H, m), 3.96~4.01 (2H, m), 6.82(1H, d, J=8Hz), 6.89~6.96(5H, m), 7.33(1H, d, J=8Hz) |
| 31 | trans | H | 2-OH-phenyl | (400MHz in D₂O) δ 3.50(1H, t, J=11Hz), 3.62(1H, m), 3.89~ 4.02(4H, m), 6.85(1H, dd, J=8Hz, 2Hz), 6.93(1H, d, J=8Hz), 6.95 (1H, d, J=2Hz,), 7.01(2H, m), 7.29 (1H, d, J=8Hz), 7.34(1H, d, J=8Hz) |
| 32 | trans | H | 3-Cl-4-OCH₃-phenyl | (400MHz in D₂O) δ 3.45(1H, m), 3.56(1H, m), 3.85~4.10(3H, m), 3.92(3H, s), 4.33(1H, m), 6.83~ 7.05(1H, m), 7.24(1H, d, J=6Hz), 7.39(1H, m) |

TABLE 4-continued

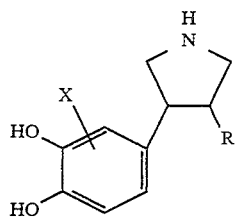

| Ex. No. | cis/trans | X | R | NMR |
|---|---|---|---|---|
| 33 | trans | H | 2-C₂H₅-tetrahydrothiophenyl | (400MHz in D₂O) δ 1.94(3H, t, J=7Hz), 2.40~2.51(2H, m), 3.50~3.63(3H, m), 3.96~4.74(3H, m), 6.85(1H, dd, J= 8Hz, 2Hz), 6.94 (1H, d, J=8Hz), 6.94 (1H, d, J=2Hz), 7.00 (1H, d, J=5Hz), 7.42(1H, d, J=5Hz) |
| 34 | trans | H | 3-Cl-2-OH-phenyl | (400MHz in D₂O) δ 3.72(1H, t, J=11Hz), 3.84(1H, t, J=11Hz), 4.07(1H, m), 4.26~ 4.44(3H, m), 7.09~ 7.33(5H, m) |
| 35 | trans | 5-Cl | 2-Cl-3-OH-phenyl | (400MHz in D₂O) δ 3.42(1H, t, J=11Hz), 3.52(1H, t, J=11Hz), 3.74(1H, ddd, J= 11Hz, 11Hz, 8Hz), 3.08(1H, dd, J=11Hz, 11Hz), 4.03(1H, dd, J=11Hz, 11Hz), 4.23(1H, ddd, J= 11Hz, 11Hz, 8Hz), 6.48(2H, s), 6.95(1H, dd, J=8Hz, 1Hz), 7.06(1H, dd, J= 8Hz, 1Hz), 7.18(1H, t, J=8Hz) |
| 36 | trans | H | benzothiophenyl | (400MHz in D₂O) δ 3.66(1H, t, J=11Hz), 3.68(1H, t, J=11Hz), 3.87(1H, ddd, J= 11Hz, 11Hz, 8Hz), 4.06(1H, dd, J=11Hz, 11Hz), 4.14(1H, dd, J=11Hz, 11Hz), 4.33(1H, ddd, J= 11Hz, 11Hz, 8Hz), 6.84(1H, d, J=8Hz), 6.84(1H, d, J=8Hz), 6.91 (1H, d, J=2Hz), 7.48(1H, d, J 32 5Hz), 7.51(1H, t, J=8Hz), 7.60(1H, d, J=8Hz), 6.67(1H, d, J=5Hz), 7.98(1H, d, J=8Hz) |
| 37 | trans | H | benzothiophenyl vinyl | (400MHz in D₂O) δ 3.63(1H, t, J=11Hz), 3.69(1H, t, J=11Hz), 3.91~4.17(4H, m), 6.75(1H, d, J=2Hz), 7.36(1H, d, J=5Hz), 7.44(1H, d, J=8Hz), 7.49~7.54(3H, m), 7.77(1H, d, J=8Hz) |

TABLE 4-continued

![structure: 3,4-dihydroxyphenyl pyrrolidine with X and R substituents]

| Ex. No. | cis/trans | X | R | NMR |
|---|---|---|---|---|
| 38 | trans | H | (pyridyl group) | (400MHz in D$_2$O) δ 3.68(1H, t, J=11Hz), 3.76(1H, dt, J=7Hz, 11Hz), 3.84(1H, t, J=11Hz), 4.06~4.15(2H, m), 4.21(1H, dd, J=8Hz, 12Hz) 6.85(1H, dd, J=2Hz, 8Hz), 6.93(1H, d, J=2Hz), 6.98(1H, d, J=8Hz), 8.00(2H, d, J=7Hz), 8.78(2H,1) |
| 39 | trans | H | (N-methylimidazolyl group, CH$_3$) | (90MHz in CDCl$_3$) δ 2.36(3H, s), 3.5~4.8 (5H, m), 5.52(1H, 6q, J=11Hz), 6.6~6.88 (3H, d, J=2Hz), 7.58(1H, d, J=2Hz), 8.04(1H, d, J=2Hz) |
| 40 | trans | H | (pyridyl group) | (400MHz in D$_2$O) δ 3.58(1H, t, J=11Hz), 3.65(1H, t, J=11Hz), 3.66~3.83(2H, m), 4.02(1H, dd, J=7Hz, 11Hz), 4.08(1H, dd, J=7Hz, 11Hz), 6.81(1H, dd, J=2Hz, 8Hz,), 7.89(1H, d, J=8Hz), 8.44(1H, s), 8.49(1H,(1H, d, J=4Hz) |

Example 41 trans-3-Benzyl-4-(3,4-dihydroxyphenyl)-pyrrolidine hydrobromide

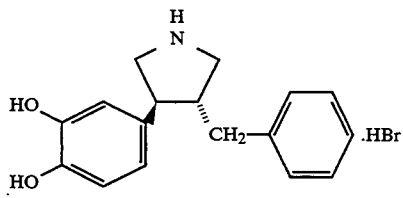

(1) Ethyl 2-benzyl-3-(3,4-dimethoxyphenyl)-4-nitrobutyrate 10 g (56.1 mmol) of ethyl phenylpropionate was dropwise added at −78° C. in 300 ml of THF to lithium diisopropylamide prepared from 9.04 ml (64.5 mmol) of diisopropylamine and 38.6 ml (64.5 mmol) of 1.6M n-butyllithium. The mixture was stirred at the same temperature for 15 min, and a solution of 11.74 g (56.1 mmol) of 2-(3,4-dimethoxyphenyl)nitroethene in 200 ml of THF was dropwise added to the mixture. Then, stirring was continued for 30 min. 20 ml of water was added to the reaction mixture to stop the reaction, and THF was distilled off in vacuo. 100 ml of a 3N hydrochloric acid solution was added to the residue, and the mixture was extracted twice with 300 ml of methylene chloride. The resultant organic layer was washed with a saturated saline solution and dried over anhydrous sodium sulfate. The solvent was distilled off in vacuo, and the residue was subjected to silica gel column chromatography (developing solvent; ethyl acetate:n-hexane=1:2) to prepare 16.55 g of an intended product (yield: 80%). In this case, the threo isomer was first eluted and next came the erythro isomer (threo:erythro=8:6). The erythro isomer was crystalline, while the threo isomer was oleaginous.

threo isomer:
NMR(90 MHz, CDCl$_3$) δ; 1.02(3H, t, J=7 Hz), 2.48~3.08(3H, m), 3.48~3.70(1H, m), 3.76(3H, s), 3.78 (3H, s), 3.95(2H, q, J=7 Hz), 4.52~4.72 (2H, m), 6.60~6.76(3H, m), 6.84~7.20 (5H, m)

erythro isomer:
NMR(90 MHz, CDCl$_3$) δ; 0.96 (3H, d, J=7 Hz), 2.76~3.20(3H, m), 3.50~3.80(1H, m), 3.82(6H, s), 3.83 (2H, q, J=7 Hz), 4.67~4.82(2H, m), 6.57~6.72(3H, m), 6.92~7.24 (5H, m)
m.p. (°C.): 94–96

(2) Ethyl threo-4-amino-2-benzyl-3-(3,4-dimethoxyphenyl)butyrate 8.1 g (20.9 mmol) of ethyl threo-2-benzyl-3-(3,4-dimethoxyphenyl)-4-nitrobutyrate was dissolved in 38 ml of ethanol, and 12.5 ml of concentrated hydrochloric acid was added to the solution. 5.47 g of powdery zinc (84 mmol) was added to the mixture in portions on a water bath. After the completion of the addition, the mixture was heated under reflux for 2 hr. The reaction mixture was concentrated, and a 10% aqueous sodium hydroxide was added thereto to basify the residue. The resulting solution was extracted three times with methylene chloride. The organic phase was washed with a saturated saline solution and dried over anhydrous sodium sulfate. The solvent was distilled off in vacuo to prepare an intended crude product. The crude product was used in the next step without isolation and purification.

(3) trans-3-Benzyl-4-(3,4-dimethoxyphenyl)-2-pyrrolidone

The crude product of ethyl threo-4-amino-2-benzyl-3-(3,4-dimethoxyphenyl)butyrate was dissolved as such in 200 ml of xylene and heated under reflux for 6 hr. Xylene was distilled off in vacuo to prepare an intended crude product. The crude product was purified from ethanol to prepare 2.55 g (yield: 39%) of an intended product.
m.p. (°C.): 116–118

NMR(90 MHz, CDCl$_3$) δ; 2.88(1H, ddd, J=5 Hz, 6 Hz, 9 Hz), 2.99(1H, dd, J=5 Hz, 14 Hz), 3.07(1H, dd, J=6 Hz, 14 Hz), 3.20(1H, dt, J=8 Hz, 9 Hz), 3.23(1H, t, J=8 Hz), 3.51(1H, t, J=8 Hz), 3.81(3H, s), 3.86(3H, s), 6.24(1H, bs), 6.55(1H, d, J=2 Hz), 6.69(1H, dd, J=2 Hz, 8 Hz), 6.79 (1H, d, J=8 Hz), 7.13~7.24(5H, m)

(4) trans-3-Benzyl-4-(3,4-dimethoxyphenyl)-pyrrolidine 10 ml of 1M borane/THF complex was added to 10 ml of a solution of 0.81 g (2.6 mmol) of trans-3-benzyl-4-(3,4-dimethoxyphenyl)-2-pyrrolidone in THF, and the mixture was heated under reflux for 6 hr. After the completion of the cooling, 10 ml of a 6N hydrochloric acid solution was dropwise added at room temperature carefully, and the mixture was stirred at 60° C. for 30 min. THF was distilled off in vacuo, and the residue was basified with a 10% aqueous sodium hydroxide solution and extracted twice with methylene chloride. The resultant organic phase was dried over anhydrous sodium sulfate, and the solvent was distilled off in vacuo to prepare a crude product. The crude product was adsorbed on silica gel to elute impurities (methylene:methanol=95:5), and elution was again conducted to prepare 0.37 g (yield: 48%) of an intended product.

(5) trans-3-Benzyl-4-(3,4-dihydroxyphenyl)-pyrrolidine hydrobromide 0.37 g (1.24 mmol) of trans-3-benzyl-4-(3,4-dimethoxyphenyl)pyrrolidine was dissolved in methylene chloride, and 10 ml of a solution of 1M boron tribromide in methylene chloride was added to the resultant solution. The solution was stirred at room temperature for 3 hr. The reaction mixture was concentrated in vacuo. Further, methylene chloride was added to the concentrate and methanol (3 ml) was dropwise added thereto. The mixture was again concentrated in vacuo. This procedure was repeated several times, and a precipitated crystal was recovered by filtration to prepare 70 mg of a hydrobromide as an intended product (yield: 16%).

m.p. (°C.): 182°–184° C.

elemantary analysis: as $C_{17}H_{19}NO_2.HBr$

|  | C | H | N |
|---|---|---|---|
| calculated (%): | 58.30 | 5.76 | 4.00 |
| found (%): | 58.56 | 5.86 | 3.79 |

NMR(D$_2$O) δ; 2.76~2.83(2H, m), 2.85~2.93(1H, m), 3.17~3.28(1H, m), 3.37(1H, t, J=12 Hz), 3.66(1H, dd, J=7 Hz, 12 Hz), 3.82(1H, dd, J=8 Hz, 12 Hz), 6.90(1H, dd, J=2 Hz, 8 Hz), 6.93(1H, d, J=2 Hz), 6.99(1H, d, J=8 Hz), 7.27(2H, d, J=8 Hz), 7.32~7.42(3H, m)

Example 42 cis-3-Benzyl-4-(3,4-dihydroxyphenyl)pyrrolidine hydrobromide

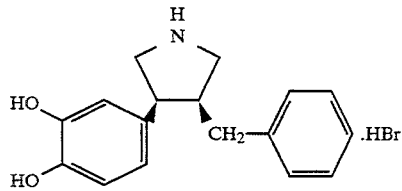

(1) Ethyl erythro-4-amino-3-benzyl-3-(3,4-dimethoxyphenyl)butyrate

The intended product was prepared in the same manner as that of the preparation of the threo isomer by making use of 6.01 g (15.51 mmol) of ethyl erythro-2-benzyl-3-(3,4-dimethoxyphenyl)-4-nitrobutyrate, 4.06 g (62.1 mmol) of powdery zinc, 28 ml of ethanol, and 9.3 ml of concentrated hydrochloric acid.

m.p. (°C.): 74–80

(2) cis-3-Benzyl-4-(3,4-dimethoxyphenyl)-2-pyrrolidone

The intended product was synthesized from the crude product of ethyl erythro-4-amino-2-benzyl-3-(3,4-dimethoxyphenyl)butyrate in the same manner as that of the preparation of the threo isomer, except that the reaction time was 12 hr. Yield was 3.18 g (66%, in two stages)

m.p. (°C.): 137–139

NMR(CDCl$_3$) δ; 2.30(1H, dd, J=11 Hz, 14 Hz), 3.11(1H, ddd, J=4 Hz, 8 Hz, 11 Hz), 3.17(1H, dd, J=4 Hz, 14 Hz), 3.42(1H, d, J=10 Hz), 3.51(1H, dd, J=7 Hz, 8 Hz), 3.73(3H, s), 3.76(1H, dd, J=7 Hz, 10 Hz), 3.88(3H, s), 6.45(1H, d, J=2 Hz), 6.70(1H, dd, J=2 Hz, 8 Hz), 6.79 (1H, d, J=8 Hz), 6.91(1H, d, J=9 Hz), 7.12~7.22(3H, m)

(3) cis-3-Benzyl-4-(3,4-dimethoxyphenyl)pyrrolidine 0.45 g (yield: 56%) of the intended product was prepared from 0.84 g (2.70 mmol) of cis-3-benzyl-4-(3,4-dimethoxyphenyl)-2-pyrrolidone in the same manner as that of the synthesis of the trans isomer.

(4) cis-3-benzyl-4-(3,4-dimethoxyphenyl)-pyrrolidine hydrobromide 0.10 g (yield: 22%) of a hydrobromide as the intended product was prepared from 0.45 g (1.51 mmol) of cis-3-benzyl-4-(3,4-dimethoxyphenyl)pyrrolidine in the same manner as that of the synthesis of the trans isomer.

NOE (7.45%) was observed between C$_3$—H and C$_4$—H.

m.p.(°C.): 209°–210 ° C. (decomposed)

elementary analysis: as $C_{17}H_{19}NO_2.HBr.H_2O$

|  | C | H | N |
|---|---|---|---|
| calculated (%): | 55.45 | 5.02 | 3.80 |
| found (%): | 55.65 | 5.65 | 3.76 |

NMR(D$_2$O) δ; 2.32(1H, dd, J=11 Hz, 14 Hz), 2.77(1H, dd, J=6 Hz, 14 Hz), 3.00~3.07(1H, m), 3.31 (1H, dd, J=7 Hz, 12 Hz), 3.49(1H, dd, J=7 Hz, 12 Hz), 3.70~3.82(2H, m), 3.88(1H, dd, J=7 Hz, 11 Hz), 6.81(1H, dd, J=2 Hz, 8 Hz), 6.85(1H, d,J=2 Hz), 7.03(1H, d, J=8 Hz), 7.19(2H, d, J=7 Hz)

Example 43 trans-3-(2-Hydroxy-3-chlorophenylmethyl)-4-(3,4-dihydroxyphenyl)pyrrolidine hydrobromide

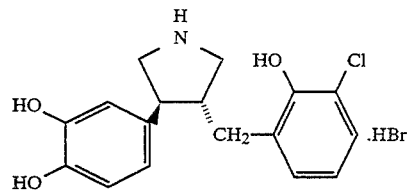

(1) 3-Chloro-2-methoxybenzyl bromide

A mixture of 20.36 g (0.13 mol) of m-chloro-o-methoxytoluene with 23.2 g (0.13 mol) of N-bromosuccinimide, 0.6 g (2.47 mmol) of benzoyl peroxide, and 200 ml of tetrachloromethane was irradiated with light (≧300 nm) from a high-pressure mercury lamp (400 W) for 5 hr by making use of a Pyrex filter. Insolubles were removed by filtration, and the filtrate was concentrated in vacuo. The residue was dissolved in methylene chloride and washed with water. The resultant methylene chloride phase was dried over anhydrous magnesium sulfate, and the solvent was distilled off in vacuo to prepare 29.2 g of the intended product as an oleaginous matter.

(2) Diethyl 2-(3-chloro-2-methoxybenzyl)malonate 100 ml of a suspension of 4.75 g (0.118 mol) of sodium hydride in THF was cooled with ice/dry ice/methanol, and 50 ml of a solution of 20.64 g (0.128 mol) of diethyl malonate in THF was added thereto in portions with stirring. 50 ml of a solution of 29.2 g (0.124 mol) of the halide prepared in the above step (1) in THF was added thereto, and the mixture was stirred at room temperature for 3 hr. The solvent was distilled off in vacuo, and the residue was diluted with methylene chloride, washed with water and then with a saline solution, and dried over anhydrous magnesium sulfate. The solvent was distilled off in vacuo, and the residue was subjected to vacuum distillation to prepare 18.8 g of the intended product having a boiling point 144° to 155° C.

(3) 3-(3-Chloro-2-methoxyphenyl)propionic acid

A mixture of 18.8 g (59.7 mmol) of a malonic acid derivative obtained in the above step (2) with 142 ml of an 8N hydrochloric acid solution was heated under reflux overnight. The reaction mixture was cooled to recover a precipitated crystal by filtration. The crystal was washed with water and dried to prepare 11.14 g of the intended product.

(4) Ethyl 3-chloro-2-methoxyphenylpropionate

A mixture of 11.14 g (51.9 mmol) of a propionic acid derivative prepared in the above step (3) with 0.96 ml of concentrated sulfuric acid and 40 ml of ethanol was heated under reflux for 2.5 hr. The solvent was distilled off in vacuo, and the residue was subjected to medium-pressure silica gel column chromatography [hexane:ethyl acetate=5:1 (v/v)] to prepare 7.37 g of the intended product as an oleaginous matter.

(5) Ethyl 2-(3-chloro-2-methoxybenzyl)-3-(3,4-dimethoxyphenyl)-4-nitrobutyrate 11.1 ml (17.8 mmol) of 1.6M n-butyllithium in hexane was added in portions to 20 ml of a solution of 2.5 ml (17.8 mmol) of diisopropylamine in THF while stirring under cooling with dry ice/acetone. 15 min after the completion of the addition, 30 ml of a solution of 4.13 g (17 mmol) of the ester prepared in the above step (4) in THF was added thereto in portions at −50° C. or below. The mixture was stirred at the same temperature for 10 min, and 100 ml of a solution of 3.55 g (17 mmol) of a nitroolefin in THF was added thereto in portions. The mixture was stirred for 30 min, and water was added to the reaction mixture. The resulting mixture was acidified with a 2N hydrochloric acid solution and extracted with methylene chloride. The methylene chloride phase was washed with a saline solution and dried over anhydrous magnesium sulfate. The solvent was distilled off in vacuo, and the residue was subjected to medium-pressure silica gel column chromatography [hexane:ethyl acetate=3:1 (v/v)] to prepare 3.8 g of the intended product as an oleaginous matter.

(6) Ethyl 4-amino-2-(3-chloro-2-methoxybenzyl)-3-(3,4-dimethoxyphenyl)butyrate 2.73 g (41.7 mmol) of zinc was added in portions to a mixture of 3.73 g (8.25 mmol) of the nitro ester prepared in the above step (5) with 5.2 ml of concentrated hydrochloric acid and 35 ml of ethanol while stirring under cooling with iced water, and the mixture was heated under reflux for 3 hr. The excess zinc was removed by filtration, and the filtrate was concentrated in vacuo. Methylene chloride was added to the residue, and the mixture was basified with a 10% sodium hydroxide solution. The basified mixture was passed through Celite to remove precipitated insolubles by filtration. The methylene chloride phase was fractionated, washed with water and then with a saline solution, and dried over anhydrous magnesium sulfate. The solvent was distilled off in vacuo to prepare 3 g of the intended product as an oleaginous matter.

(7) 3-(3-Chloro-2-methoxybenzyl)-4-(3,4-dimethoxyphenyl)-2-pyrrolidone 30 ml of a solution of 3 g (7.1 mmol) of the amino ester prepared in the above step (6) in xylene was heated under reflux for 4 hr. The solvent was distilled off in vacuo, and the residue was subjected to medium-pressure silica gel column chromatography [chloroform:methanol=99:1 (v/v) ] to prepare 1.87 g of the intended product as an oleaginous matter.

(8) trans-3-(3-Chloro-2-methoxybenzyl)-4-(3,4-dimethoxyphenyl)-2-pyrrolidone

A mixture of 1.85 g (4.92 mmol) of the lactam prepared in the above step (7) with 2.76 g (24.6 mmol) of tert-BuOK, 30 ml of ethanol and 30 ml of xylene was heated under reflux overnight. The solvent was distilled off in vacuo. Methylene chloride was added to the residue, and the mixture was acidified with a 2N hydrochloric acid solution. The methylene chloride phase was fractionated, washed with water and then with a saline solution, and dried over anhydrous magnesium sulfate. The solvent was distilled off in vacuo, and the residue was subjected to medium-pressure silica gel column chromatography [chloroform:methanol=99:1 (v/v)] to prepare 1.06 g of the intended product as an oleaginous matter.

(9) 3-(3-Chloro-2-methoxybenzyl)-4-(3,4-dimethoxyphenyl)pyrrolidine 30 ml of a solution of 1.06 g (2.82 mmol) of the trans pyrrolidone prepared in the above step (8) in THF was added in a stream of nitrogen to 10 ml (10 mmol) of a solution of 1M $BH_3$/THF complex in THF while stirring under cooling with iced water, and the mixture was heated under reflux overnight. A 6N hydrochloric acid solution was carefully added to the reaction mixture while stirring under cooling with iced water until bubbling ceased, and the mixture was heated under reflux for 2 hr. The solvent was distilled off in vacuo, and methylene chloride was added to the residue. The mixture was basified with a 10% aqueous sodium hydroxide solution. The methylene chloride phase was fractionated, washed with a saline solution, and dried over anhydrous magnesium sulfate. The solvent was distilled off in vacuo, and the residue was subjected to medium-pressure silica gel column chromatography. Elution was conducted first with a mixture of chloroform with methanol in a chloroform to methanol ratio of 97:3 (v/v) and then with methanol only. 510 mg of the intended product was obtained as an oleaginous matter from the fraction eluted with methanol.

(10) trans-3-(2-Hydroxy-3-chlorophenyl)-4-(3,4-dihydroxyphenyl)pyrrolidine hydrobromide 6.5 ml (6.5 mmol) of a solution of 1M boron tribromide in methylene chloride was added in portions to 30 ml of a solution of 510 mg (1.41 mmol) of the pyrrolidine prepared in the above step (9) in methylene chloride in a stream of nitrogen while stirring under cooling with iced water. Subsequently, the mixture was stirred at room temperature for 4.5 hr. The solvent was distilled off in vacuo, and methanol was added in portions to the residue while stirring under cooling with iced water. Methanol was distilled off in vacuo, and an ethanol/hexane mixture was added to the residue. The mixture was allowed to stand at room temperature. A precipitated crystal was recrystallized from acetonitrile/benzene to prepare 250 mg of the intended substance.

m.p, (°C.): 207–209 elementary analysis: as $C_{17}H_{18}NO_3Cl \cdot HBr$

|  | C | H | N |
| --- | --- | --- | --- |
| calculated (%): | 50.75 | 4.79 | 3.49 |
| found (%): | 51.02 | 4.70 | 3.32 |

NMR(D₂O) δ; 2.77~2.83(1H, m), 2.94~3.03(2H, m), 3.13~3.31(3H, m), 3.74~3.82(2H, m), 6.72~6.76(2H, m), 6.83~6.87(2H, m), 7.09(1H, d, J=8 Hz), 7.23(1H, dd, J=2 Hz, 8 Hz)

Example 44

(±)-trans-3-(3,5-Difluoro-2-hydroxybenzyl)-4-(3,4-dihydroxyphenyl)pyrrolidine hydrobromide

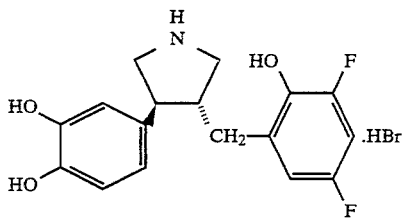

(1) 3,5-Difluoro-2-hydroxy-N,N-dimethylbenzylamine 51.72 g (0.40 mol) of 2,4-difluorophenol was dissolved in 46 ml of ethanol, and 91 ml of a 50% aqueous dimethylamine solution and 40 ml of a 37% formalin solution were added to the solution. The mixture was heated under reflux for 3 hr. After cooling the reaction mixture, extraction was conducted with ethyl acetate. The extract was washed with water and then with a saturated saline solution and dried over anhydrous sodium sulfate. The solvent was distilled off in vacuo to prepare 76 g (quantitative) of the intended product.

m.p. (°C.): 63°-64° C. (EtOH)

NMR(90 MHz, CDCl₃) δ; 2.27(6H, s), 3.55(2H, s), 6.23~6.78 (2H, m), 10.79(1H, s)

(2) 3,5-Difluoro-2-hydroxy-N,N,N-trimethylbenzylammonium iodide 74 g (0.40 mol) of 3,5-difluoro-2-hydroxy-N,N-dimethylbenzylamine was dissolved in 300 ml of chloroform, and 200 ml of methyl iodide was added thereto. The mixture was heated under reflux for 3 hr to deposit a yellow precipitate. The precipitate was recovered by filtration to prepare 114 g (yield: 87%) of the intended product.

m.p. (°C.): 170°-173° C.

(3) 3,5-Difluoro-2-hydroxybenzaldehyde 114 g (0.35 mol) of 3,5-difluoro-2-hydroxy-N,N,N-trimethylammonium iodide was dissolved in 714 ml of a 50% acetic acid solution, and 214 g (1.53 mol) of hexamethylenetetramine was dropwise added thereto. After the completion of the addition, the reaction mixture was heated under reflux for 3 hr. A 3N hydrochloric acid solution was added thereto, and the mixture was heated for 5 min. The mixture was extracted with ether and dried over anhydrous sodium sulfate, and the solvent was distilled off in vacuo to prepare a crude product. Part of the crude product was sufficiently dried, while the remainder was used as such for the subsequent reaction.

m.p. (°C.): 89°-90° C.

NMR(90 MHz, CDCl₃) δ; 7.07(1H, s), 7.15(1H, s), 9.87(1H, d, J=1.8 Hz), 10.70(1H, bs)

(4) 3,5-Difluoro-2-methoxybenzaldehyde 3,5-Difluoro-2-hydroxybenzaldehyde in the form of a crude product (corresponding to 0.35 mol) was dissolved in 800 ml of acetonitrile. 110 g (0.8 mol) of potassium carbonate and 61 ml (0.96 mol) of methyl iodide were added thereto, and the mixture was heated under reflux for 5 hr. After cooling the mixture, insolubles were removed by filtration, and the mother liquor was concentrated. 1.3 l of ether was added to the concentrate, and the mixture was washed twice with 500 ml of water. Then, the mixture was washed with a saturated saline solution, and the ether layer was dried over anhydrous magnesium sulfate. The solvent was distilled off in vacuo to prepare 39.6 g (yield: 66%) of the intended product (in two states).

m.p. (°C.): 37°-39° C.

NMR(90 MHz, CDCl₃) δ; 4.02(3H, d, J=2 Hz), 6.78~7.29(3H, m), 10.23(1 H, 4 Hz)

(5) 3,5-Difluoro-2-methoxybenzyl alcohol 39.6 g (0.23 mol) of 3,5-difluoro-2-methoxybenzaldehyde was dissolved in 80 ml of ethanol, and 35 ml of a solution of 4.35 g (0.115 mol) of sodium borohydride in ethanol was dropwise added thereto at 0° C. over a period of 5 min. The mixture was stirred at room temperature for 1 hr, and 115 ml of water was added thereto to stop the reaction. The reaction mixture was extracted four times with 115 ml of ether. The extract was washed with a saline solution and dried over anhydrous magnesium sulfate. Ether was distilled off in vacuo, and the crude product thus obtained was distilled to prepare 21.2 g (yield: 53%) of the intended product.

b.p.: 108°-110° C./2 mmHg

NMR(90 MHz, CDCl₃) δ; 2.60(1H, br), 3.88(3H, d, J=2 Hz), 3.63 (2H, s), 6.57~6.92(2H, m)

(6) 3,5-Difluoro-2-methoxybenzyl chloride 10 g (57.4 mmol) of 3,5-difluoro-5-methoxybenzyl alcohol was dissolved in 100 ml of methylene chloride. 25 ml (287 mmol) of thionyl chloride and 7 drops of dimethylformamide were added thereto, and the mixture was heated under reflux for 1 hr. The reaction mixture was cooled, concentrated, and subjected to azeotropic distillation twice with benzene. The residue was dissolved in ether, washed twice with water and then with a saline solution, and dried over anhydrous magnesium sulfate. The solvent was distilled off in vacuo, and the oleaginous matter thus obtained was distilled to prepare 9.72 g (yield: 88%) of the intended product (97°-98° C.)/24-25 mmHg).

H-NMR(90 MHz, CDCl₃) δ; 3.95(3H, d, J=2 Hz), 4.58(2H, s), 6.60~6.90(2H, m) m/z ; 192

(7) diethyl 2-(3,4-dimethoxybenzylidene)malonate 200 g (1.2 mol) of veratraldehyde and 220 ml (1.4 mol) of diethyl malonate were heated under reflux in 400 ml of benzene in the presence of 12 ml of pyrrolidine and 6.6 g of veratric acid for 6 hr. After cooling the reaction mixture, 700 ml of ethyl acetate was added thereto, and the mixture was washed with water. The organic phase was further washed with diluted hydrochloric acid, a saturated aqueous sodium hydrogencarbonate solution and a saline solution sequentially and dried over anhydrous magnesium sulfate. The solvent was distilled off in vacuo, and the residue was distilled to prepare 360.0 g (yield: 97%) of the intended product (b.p.: 193°-200° C./0.5-2.0 mmHg).

(8) Ethyl 3-cyano-3-(3,4-dimethoxyphenyl)-propionate

A solution of 40.4 g (0.61 mol) of potassium cyanide in 72 ml of water was added to 1.44 l of a solution of 180.0 g (0.58 mol) of the diester (7) in ethanol, and the mixture was stirred at 70° C. for 10 hr. The reaction mixture was cooled and concentrated. 0.5 l of water and 1.5 l of ethyl acetate were added thereto, and the resultant organic phase was separated from the mixture. The organic phase was washed with water and then with a saturated saline solution, and dried over anhydrous magnesium sulfate. The solvent was distilled off in vacuo to prepare 201 g (0.76 mol) (yield: 66%) of the intended product.

(9) 4-(3,4-Dimethoxyphenyl)-2-pyrrolidone 100.5 g of the cyano ester (8) was hydrogenated at 100° C. for 24 hr in a hydrogen atomsphere of 50 kg/cm$^2$ in the presence of Raney cobalt in an amount of about 50 ml per 1 of ethanol. After the removal of the catalyst, the solvent was distilled off in vacuo, and the residue was recrystallized from ethanol to prepare 53.5 g (yield: 64%) of the intended product.

(10) 1-(3,4-Dimethoxybenzyl)-4-(3,4-dimethoxyphenyl)-2-pyrrolidone 30 g (0.136M) of the pyrrolidone (9) was treated with Triton B (60 ml of a 40% methanol solution in 400 ml of benzene. Benzene was distilled off in vacuo, and 400 ml of benzene was again added to the residue. This procedure was repeated three times, and 25.31 g of 3,4-dimethoxybenzyl chloride was added thereto at room temperature. The mixture was stirred at 60° C. for 6 hr, and water was added to the reaction mixture. The resultant organic phase was separated and washed twice with water and once with a saturated saline solution. The organic phase was dried over anhydrous sodium sulfate, and the solvent was distilled off in vacuo. The residue was recrystallized from ethanol to prepare 41.54 g (yield: 82%) of the intended product.

m.p. (°C.): 117–118

NMR(90 MHz, CDCl$_3$) δ; 2.40~2.80(2H, m), 2.80~3.60(3H, m), 3.74~3.82(12H, m), 4.40(2H, s), 6.54~6.76(6H, m)

(11) 3-(3,5-Difluoro-2-methoxybenzyl)-N-(3,4-dimethoxybenzyl)-4-(3,4-dimethoxyphenyl)-2-pyrrolidone 2.1 ml (15 mmol) of diisopropylamine was dissolved in 30 ml of THF in a nitrogen atmosphere. 9.4 ml (15 mmol) of 1.6M n-butyllithim was dropwise added thereto at −78° C., and the mixture was allowed to stand at the same temperature for 10 min. 100 ml of a solution of 3.71 g (10 mmol) of N-(3,4-dimethoxybenzyl)-4-(3,4-dimethoxyphenyl)-2-pyrrolidone in THF was dropwise added to this solution at −78° C. The mixture was stirred for 30 min, and 10 ml of water was added thereto to stop the reaction. The reaction mixture was concentrated, and methylene chloride was added to the residue. The mixture was washed with water and then with a saline solution, and the organic phase was dried over anhydrous sodium sulfate. The solvent was distilled off in vacuo, and the crude product thus obtained was subjected to silica gel column chromatography (developing solvent; ethyl acetate: n-hexane=3:1) to prepare 4.65 g (yield: 88%) of the intended product.

m.p. (°C.): 94–96

(12) 3-(3,5-Difluoro-2-methoxybenzyl)-N-(3,4-dimethoxybenzyl)-4-(3,4-dimethoxyphenyl)pyrrolidine 200 ml of a solution of 17.78 g (33.8 mmol) of 3-(3,5-difluoro-2-methoxybenzyl)-N-(3,4-dimethoxybenzyl)-4-(3,4-dimethoxyphenyl)pyrrolidone in THF was dropwise added at 0° C. in a nitrogen atmosphere to 150 ml of a 1M solution of a borane/THF complex in THF. The mixture was heated under reflux for 2 hr and cooled, and 50 ml of a 6N hydrochloric acid solution was added thereto. The mixture was heated to 60° C. After stirring for 2 hr, THF was concentrated in vacuo and extracted twice with methylene chloride. The obtained organic phase was washed with a saline solution and dried over anhydrous sodium sulfate, and the solvent was distilled off in vacuo. The residue was subjected to silica gel column chromatography (ethyl acetate:n-hexane=4:1) to prepare 12.46 g (yield: 72%) of the intended product.

(13) 3-(3,5-Difluoro-2-methoxybenzyl)-4-(3,4-dimethoxyphenyl)pyrrolidine 2.5 g (5.9 mmol) of 3-(3,5-difluoro-2-methoxybenzyl)-N-(3,4-dimethoxybenzyl)-4-(3,4-dimethoxyphenol)pyrrolidine was dissolved in ethanol and heated under reflux for 10 hr in the presence of 0.4 g of 10% palladium/carbon. The crude product thus prepared was subjected to silica gel column chromatography (eluted first with a mixture of methanol with methylene chloride in a methanol to methylene chloride ratio of 5:95 and then with methanol only) to prepare 1.07 g (yield: 63%) of the intended product.

(14) (±)-trans-3-(3,5-Difluoro-2-hydroxybenzyl)-4-(3,4-dihydroxyphenyl)pyrrolidine hydrobromide Concentrated hydrobromic acid was added to 1.06 g of 3-(3,5-difluoro-2-methoxy)-4-(3,4-dimethoxyphenyl)-pyrrolidine, and the mixture was stirred at 100° C. for 12 hr on an oil bath. The solvent was distilled off in vacuo and benzene was added to the residue to conduct azeotropic distillation twice. Acetonitrile was added to the residue to effect crystallization. The crystal thus formed was recovered by filtration to prepare 0.76 g (yield: 63%) of the intended product, m.p. (°C.): 217–219

NMR(D$_2$O) δ; 2.79(1H, ddd, J=5 Hz, 10 Hz, 10 Hz), 2.95~3.02(2H, m), 3.16~3.23(1H, m), 3.29(2H, dd, J=12 Hz, 23 Hz), 3.77~3.83(2H, m), 6.71~6.89(5H, m)

elementary analysis: as C$_{17}$H$_{17}$F$_2$NO$_3$.HBr

|  | C | H | N |
| --- | --- | --- | --- |
| calculated (%): | 50.76 | 4.51 | 3.48 |
| found (%): | 50.57 | 4.45 | 3.36 |

Example 45

(−)-trans-3-(3,5-Difluoro-2-hydroxybenzyl)-4-(3,4,dihydrophenyl)pyrrolidine hydrobromide (1) trans-N-Acetyl-3-(3,5-difluoro-2-methoxybenzyl)-4-(3,4-dimethoxyphenyl)-pyrrolidine 2.17 g (6.17 mmol) of trans-3-(3,5-difluoro-2-methoxybenzyl)-4-(3,4-dimethoxyphenyl)pyrrolidine prepared in step (13) of Example 4 was dissolved in 30 ml of chloroform, and 0.75 g (7.4 mmol) of triethylamine was added thereto. 10 ml of a solution of 0.5 ml (7.0 mmol) of acetyl chloride in chloroform was dropwise added thereto under cooling with ice, and the mixture was stirred at room temperature for 3 hr. 1 ml of water was added thereto to stop the reaction. The reaction mixture was washed with water, a 2N hydrochloric acid solution, and a saturated aqueous sodium hydrogencarbonate solution sequentially, and dried over anhydrous sodium sulfate. The solvent was distilled off in vacuo, and the residue was subjected to silica gel column chromatography (methylene chloride:methanol=97:3) to prepare 2.5 g (quantitative) of the intended product.

(2) 2.5 g of the above-described acetylpyrrolidine derivative was loaded on a column for separating optical isomers (Chiralcel OD; a product of Daicel Chemical Industries, Ltd.) and separated and purified by making use of a mixed solvent comprising n-hexane, isopropyl alcohol, and diethylamine (5:2:0.005) as an eluent, thereby preparing 1.06 g of the (+) isomer {[α]$_D$28: +20.2° (C=1.05 in MeOH)} and 1.09 g of the (−) isomer {[α]$_D$28: −20.1° (C=1.05 in MeOH)}.

(3) 1.09 g of the above-described (−) isomer was heated under reflux in a 47% hydrobromic acid solution for 20 hr. Hydrobromic acid was distilled off in vacuo and benzene was added to the residue to conduct azeotropic distillation twice. The residue was dissolved in ethanol, treated with activated carbon, and recovered by filtration. The solvent was distilled off in vacuo from the filtrate to prepare 1.05 g of (−)-trans-3-(3,5-difluoro-2-hydroxybenzyl)-4-(3,4-dihydroxyphenyl)-pyrrolidine hydrobromide.

$[\alpha]_D 28$: −18.5° (C=1.05 in MeOH)

The (+) isomer prepared in the above step (2) of Example 5 was treated in the same manner as that of the above step (3) to prepare (+)-trans-3-(3,5-difluoro-2-hydroxybenzyl)-4-(3,4-dihydroxyphenyl)pyrrolidine hydrobromide.

$[\alpha]_D 28$: +16.6° (C=1.01 in MeOH)

Examples 46 to 70

Pyrrolidine derivatives listed in the following Table 2 were prepared according to the above-described methods.

TABLE 3

| Ex. No. | cis/trans | X | Y | R | Z | m.p. (°C.) | molecular formula | NMR elem. anal. |
|---|---|---|---|---|---|---|---|---|
| 46 | trans | H | CH$_2$ | 2-CF$_3$-phenyl | Br | 226~227 | C$_{18}$H$_{21}$NO$_2$·HBr | H-NMR(400 MHz, D$_2$O) δ; 2.21(3H, s), 2.72~2.81(2H, m), 2.93(1H, q, J=8Hz), 3.23~3.31(2H, m), 3.37(1H, t, J=12Hz), 3.65(1H, dd, J=12Hz, 12Hz), 3.84(1H, dd, J=12Hz, 12Hz), 6.91(1H, dd, J=2Hz, 8Hz), 6.92(1H, d, J=2Hz), 6.98 (1H, d, J=8Hz), 7.22~7.25(4H, m) |

| elem. anal. | C | H | N |
|---|---|---|---|
| calcd. (%) | 59.35 | 6.08 | 3.84 |
| found (%) | 59.09 | 6.03 | 3.62 |

| Ex. No. | cis/trans | X | Y | R | Z | m.p. (°C.) | molecular formula | NMR elem. anal. |
|---|---|---|---|---|---|---|---|---|
| 47 | cis | H | CH$_2$ | 2-Me-phenyl | Br | 256~259 (dec.) | C$_{18}$H$_{21}$NO$_2$·HBr | H-NMR(400MHz, D$_2$O) δ; 2.19(3H, s), 2.31(1H, dd, J=14Hz), 2.60(1H, dd, J=14Hz), 3.03~3.09(1H, m), 3.38(1H, dd, J=12Hz, 12Hz), 3.50(1H, dd, J=12Hz, 12Hz), 3.74~3.93(3H, m), 6.82(1H, dd, J=2Hz, 8Hz), 6.86(1H, d, J=2Hz), 7.03 (1H, d, J=8Hz), 7.21~7.30(4H, m) |

| elem. anal. | C | H | N |
|---|---|---|---|
| calcd. (%) | 59.35 | 6.08 | 3.84 |
| found (%) | 59.19 | 6.10 | 3.85 |

| Ex. No. | cis/trans | X | Y | R | Z | m.p. (°C.) | molecular formula | NMR elem. anal. |
|---|---|---|---|---|---|---|---|---|
| 48 | trans | H | CH$_2$ | 2-Cl-phenyl | Br | 229~231 | C$_{17}$H$_{18}$ClNO$_2$·HBr | H-NMR(400MHz, D$_2$O) δ; 2.94~3.03(3H, m), 3.21~3.35(3H, m), 3.72(1H, dd, J=12Hz), 3.82(1H, dd, J=11Hz), 6.82~6.85(2H, m), 6.90(1H, d, J=8Hz), 7.22~7.30(3H, m), 7.36~7.40(1H, m) |

| elem. anal. | C | H | N |
|---|---|---|---|
| calcd. (%) | 53.08 | 4.98 | 3.64 |
| found (%) | 53.04 | 4.98 | 3.42 |

TABLE 3-continued

| Ex. No. | cis/ trans | X | Y | R | Z | m.p. (°C.) | molecular formula | NMR elem. anal. |
|---|---|---|---|---|---|---|---|---|
| 49 | cis | H | CH$_2$ | 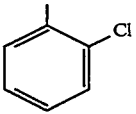 | Br | 247~148 | C$_{17}$H$_{18}$ClNO$_2$.HBr | H-NMR(40MHz, D$_2$O) δ; 2.43(1H, dd, J=14Hz, 14Hz), 2.71((1H, dd, J=14Hz, 14Hz), 3.15~3.21 3.21(1H, m), 3.39(1H, dd, J=12Hz, 12Hz), 3.51(1H, dd, J= 12Hz, 12Hz), 3.74~3.92(3H, m), 6.82(1H, dd, J=2Hz, 8Hz), 6.87(1H, d, J=2Hz), 7.00(1H, d, J=8Hz), 7.22~7.25(1H, m), 7.32~7.35(1H, m), 7.47~7.49(1H, m) |

| elem. anal. | C | H | N |
|---|---|---|---|
| calcd. (%) | 53.08 | 4.98 | 3.64 |
| found (%) | 52.82 | 4.85 | 3.68 |

| 50 | trans | H | CH$_2$ | 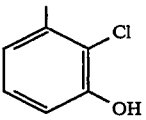 | Br | 226~227 | C$_{17}$H$_{18}$ClNO$_3$.HBr | H-NMR(400MHz, D$_2$O) δ; 2.92~3.05(3H, m), 3.20~ 3.33(3H, m), 3.75(1H, dd, J= 12Hz, 12Hz), 3.81(1H, dd, J=11Hz, 11Hz), 6.79~6.83(2H, m), 6.85~6.90(3H, m), 7.11(1H, t, J=8Hz) |

| elem. anal. | C | H | N |
|---|---|---|---|
| calcd. (%) | 50.95 | 4.79 | 3.49 |
| found (%) | 50.96 | 4.71 | 3.21 |

| 51 | trans | H | CH$_2$ | 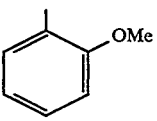 | Cl | amorphous | C$_{18}$H$_{21}$NO$_3$.HCl | H-NMR(400MHz, D$_2$O) δ; 2.82~2.97(3H, m), 3.14~ 3.33(3H, m), 3.69(1H, dd, J=12Hz, 12Hz), 3.78~ 3.83(1H, m), 3.83(3H, s), 6.80(1H, dd, J= 2Hz, 8Hz), 6.82(1H, s), 6.93(1H, d, J=8Hz), 6.96(1H, d, J=8Hz), 6.99(1H, t, J=8Hz), 7.22(1H, dd, J=2Hz, 8Hz), 7.32(1H, dt, J=2Hz, 8Hz) |
| 52 | trans | H | CH$_2$ | 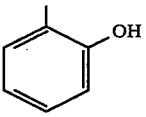 | Br | amorphouse | C$_{17}$H$_{19}$NO$_3$.HBr | H-NMR(400MHz, D$_2$O) δ; 2.77~3.03(3H, m), 3.15~ 3.41(3H, m), 3.64~3.95(2H, m), 6.74~7.02(5H, m), 7.12~7.27(2H, m) |
| 53 | cis | H | CH$_2$ | 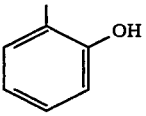 | Br | amorphouse | C$_{17}$H$_{19}$NO$_3$.HBr | H-NMR(400MHz, D$_2$O) δ; 2.31(1H, dd, J=14Hz, 14Hz), 2.52 (1H, dd, J=14Hz, 14Hz), 3.08~3.13(1H, m), 3.36(1H, dd, J=12Hz, 12Hz,), 3.47(1H, dd, J=12Hz, 12Hz)3.72~3.90 (3H, m), 6.81(1H, dd, J=2Hz, 8Hz), 6.88(1H, d, J= 2Hz), 6.9 6(1H, d, J=8Hz), 6.97(1H, t, J=8Hz), 7.01(1H, d, J=8Hz), 7.10(1H, d, J=8Hz), 7.25(1H, dt, J=1Hz, 8Hz) |

TABLE 3-continued

| Ex. No. | cis/ trans | X | Y | R | Z | m.p. (°C.) | molecular formula | NMR elem. anal. |
|---|---|---|---|---|---|---|---|---|
| 54 | cis | H | $CH_2$ | 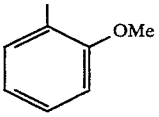 | Cl | amorphouse | $C_{18}H_{21}NO_3 \cdot HCl$ | H-NMR(400MHz, $D_2O$) δ; 2.30(1H, dd, J=14Hz, 14Hz), 2.56(1H, dd, J=14Hz, 14Hz), 3.08~3.10(1H, m), 3.35(1H, dd, J=12Hz, 12Hz), 3.47(1H, dd, J=12Hz, 12Hz), 3.70~3.83(3H, m), 3.87(3H, s), 6.80(1H, d, J=8Hz), 6.85(1H, d, J=2Hz ), 7.02(1H, d, J=8Hz), 7.04(1H, t, J=8Hz), 7.08(1H, d, J=8Hz), 7.16(1H, d, J=8Hz), 7.37(1H, t, J=8Hz) |
| 55 | trans | H | $CH_2$ |  | Cl | amorphouse | $C_{15}H_{17}NO_2S \cdot HCl$ | H-NMR(400MHz, $D_2O$) δ; 2.70~2.80(3H, m), 3.10~ 3.19(2H, m), 3.34(1H, t, J=12Hz), 3.67(1H, dd, J=12Hz, 12Hz), 3.78 (1H, dd, J=12Hz, 12Hz), 6.83 (1H, dd, J=2Hz, 8Hz), 6.88~ 6.91(2H, m), 6.98(1H, d, J= 8Hz), 7.05(1H, d, J=2 Hz), 7.37 (1H, dd, J=5Hz, 5Hz) |
| 56 | trans | H | $CH_2$ | 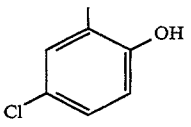 | Br | amorphouse | $C_{17}H_{18}ClNO_3 \cdot HBr$ | H-NMR(400MHz, $D_2O$) δ; 2.67(1H, dd, J=14Hz, 14Hz), 2.85~2.94(2H, m), 3.12~3.31(3H, m), 3.77(1H, d, J=12Hz), 6.73(1H, d, J= 8Hz), 6.75(1H, dd, J=2Hz, 8Hz), 6.77(1H, d, J= 2Hz), 6.87(1H, d, J=8Hz), 7.02(1H, d, J=3Hz), 7.06(1H, dd, J=3Hz, 8Hz) |
| 57 | trans | H | $CH_2$ | 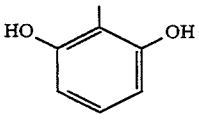 | Br | amorphouse | $C_{17}H_{19}NO_4 \cdot HBr$ | H-NMR(400MHz, $D_2O$) δ; 2.83~3.02(3H, m), 3.20~ 3.27(2H, m), 3.32(1H, t, J= 12Hz), 3.70~3.84(2H, m), 6.44(2H, d, J=8Hz), 6.83(1H, dd, J=2Hz, 8Hz), 6.86(1H, d, J=2Hz), 6.89(1H, d, J=8Hz), 6.99(1H, t, J=8Hz) |
| 58 | cis | H | $CH_2$ | 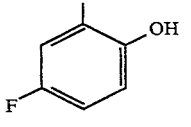 | Br | amorphouse | $C_{17}H_{18}FNO_3 \cdot HBr$ | H-NMR(400MHz, $D_2O$) δ; 2.34(1H, dd, J=14Hz, 14Hz), 2.50(1H, dd, J=14Hz, 14Hz), 3.11~3.17(1H, m), 3.36(1H, dd, J=12Hz, 12Hz), 3.53(1H, dd, J=12Hz, 12Hz), 3.72~3.90(3H, m), 6.77~ 6.90(6H, m), 6.93(1H, dd, J=3Hz, 8Hz), 6.99(1H, d, J=8Hz) |
| 59 | trans | H | $CH_2$ | 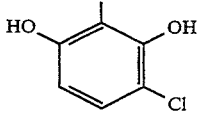 | Br | amorphouse | $C_{17}H_{18}FNO_3 \cdot HBr$ | H-NMR(400MHz, $D_2O$) δ; 2.69(1H, dd, J= 14Hz, 14Hz), 2.81(1H, dd, J= 14Hz, 14Hz), 2.88~2.94(1H, m), 3.13~3.32(3H, m), 3.72(1H, dd, J=12Hz, 12Hz), 3.79(1H, dd, J=12Hz, 12Hz), 6.72~6.90(6H, m) |
| 60 | trans | H | $CH_2$ | 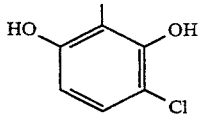 | Br | amorphouse | $C_{17}H_{18}ClNO_4 \cdot HBr$ | H-NMR(400MHz, $D_2O$) δ; 2.85~3.09(3H, m), 3.16~ 3.33(3H, m), 3.76~ 3.83(2H, m), 6.39(1H, d, J=9Hz), 6.72~6.77(2H, m), 6.84(1H, d, J=9Hz), 7.03(1H, d, J=9Hz) |

TABLE 3-continued

| Ex. No. | cis/ trans | X | Y | R | Z | m.p. (°C.) | molecular formula | NMR elem. anal. |
|---|---|---|---|---|---|---|---|---|
| 61 | trans | H | CH$_2$ | 3-hydroxyphenyl | Br | amorphouse | C$_{17}$H$_{19}$NO$_3$.HBr | H-NMR(400MHz, D$_2$O) δ; 2.69~2.78(3H, m), 3.10~3.23(2H, m), 3.33(1H, t, J=12Hz), 3.65(1H, dd, J=7Hz, 12Hz), 3.74~3.81(2H, m), 6.67(1H, d, J=2Hz), 6.75~6.79(2H, m), 6.83(1H, dd, J=2Hz, 8Hz), 6.86(1H, d, J=3Hz), 6.95(1H, d, J=8Hz), 7.22(1H, t, J=8Hz) |
| 62 | trans | H | CH$_2$ | 3-chlorophenyl | Br | 220~222 (dec.) | C$_{17}$H$_{19}$ClNO$_2$.HBr | H-NMR(400MHz, D$_2$O) δ; 2.77~2.95(3H, m), 3.18(1H, m), 3.23(1H, dd, J=11Hz, 21Hz), 3.35(1H, t, J=11Hz), 3.74(1H, dd, J=7.3Hz, 12Hz), 3.82(1H, dd, J=8Hz, 12Hz), 6.78~6.81(2H, m), 6.91(1H, d, J=9Hz), 7.14~7.17(2H, m), 7.25~7.31 (2H, m)<br><br>elem. anal.  C    H    N<br>calcd. (%) 53.08 4.98 3.64<br>found (%)  53.04 4.90 3.55 |
| 63 | trans | H | CH$_2$ | 2-fluoro-4-hydroxyphenyl | Br | amorphouse | C$_{17}$H$_{18}$FNO$_3$.HBr.2H$_2$O | H-NMR(400MHz, D$_2$O) δ; 2.72~2.86(3H, m), 3.13~3.26(2H, m), 3.31(1H, t, J=5.5Hz), 3.74(1H, dd, J=5.5Hz, 12Hz), 3.81(1H, dd, J=8Hz, 12Hz), 6.75~6.97(6H, m)<br><br>elem. anal.  C    H    N<br>calcd. (%) 48.58 5.52 3.33<br>found (%)  48.71 5.03 3.05 |
| 64 | trans | H | NH | phenyl | Br | amorphouse | C$_{16}$H$_{18}$N$_2$O$_2$.HBr | H-NMR(400MHz, D$_2$O) δ; 3.40(1H, dd, J=8Hz, 12Hz), 3.54(1H, m), 3.95(1H, dd, J=14Hz, 18Hz), 4.07(1H, dd, J=8Hz, 12Hz), 4.54(1H, dd, J=8Hz, 16Hz), 6.90~6.98(5H, m), 7.05(1H, t, J=7Hz), 7.35(2H, m) |
| 65 | trans | H | O | phenyl | Cl | amorphouse | C$_{16}$H$_{17}$NO$_3$.HCl | H-NMR(400MHz, D$_2$O) δ; 3.57(1H, dd, J=8Hz, 12Hz), 3.67~3.70(2H, m), 3.85(1H, dd, J=5Hz, 13Hz), 3.97(1H, dd, J=8Hz, 12Hz), 5.09~5.11(1H, m), 6.80(1H, dd, J=2Hz, 8Hz), 6.90(1H, d, J=12Hz), 6.97~7.00(3H, m), 7.14(1H, t, J=7Hz), 7.41(2H, t, J=7Hz) |
| 66 | trans | H | CH$_2$ | 4-hydroxyphenyl | Br | 236~238 (dec.) | C$_{17}$H$_{19}$NO$_3$.HBr.½H$_2$O | H-NMR(90MHz, CD$_3$OD) δ; 2.25~3.75(8H, m), 6.52~6.95(7H, m)<br><br>elem. anal.  C    H    N<br>calcd. (%) 54.39 5.65 3.73<br>found (%)  54.33 5.38 3.71 |
| 67 | trans | H | —S— | phenyl | Cl | 209 | C$_{16}$H$_{17}$NO$_2$S.HCl | H-NMR(400MHz, D$_2$O) δ; 3.37~3.51(3H, m), 3.86~3.89(1H, m), 4.00~4.04(2H, m), 6.89(1H, dd, J=2.5Hz, 8.1Hz), 6.92(1H, d, J=2.5Hz), 6.98(1H, d, J=8.1Hz), 7.43~7.50(5H, m)<br>elem. anal.  C    H    N<br>calcd. (%) 59.33 5.61 4.33<br>found (%)  59.46 5.57 4.47 |

TABLE 3-continued

| Ex. No. | cis/ trans | X | Y | R | Z | m.p. (°C.) | molecular formula | NMR elem. anal. |
|---|---|---|---|---|---|---|---|---|
| 68 | trans | H | -S(=O)(=O)- | phenyl | Cl | 270 (dec.) | $C_{16}H_{17}NO_4S \cdot HCl$ | H-NMR(400MHz, $D_2O$) δ; 3.43(1H, t, J=12Hz), 3.74~3.81(1H, m), 3.96(1H, dd, J=8Hz, 12Hz), 4.15~4.17(2H, m), 4.65~4.72(1H, m), 6.54(1H, d, J=2Hz), 6.65 (1H, dd, J=2Hz, 8Hz), 6.78(1H, d, J=8Hz), 7.57(2H, dd, J=7Hz, 7Hz), 7.76(1H, dd, J=7Hz, 8Hz), 7.83(2H, d, J=8Hz) elem. anal. C H N calcd. (%) 53.68 5.64 3.91 found (%) 53.85 5.18 3.75 |
| 69 | trans | H | $CH_2$ | 2-thienyl | Br | 165~168 (dec.) | $C_{15}H_{17}NO_2S \cdot HBr$ | H-NMR(400MHz, $CD_3OD$) δ; 2.68(1H, br), 2.87(1H, dd, J=10Hz, 15Hz), 3.03~3.17(3H, m), 3.26(1H, t, J=11Hz), 3.56(1H, dd, J=9Hz, 12Hz), 3.68(1H, dd, J= 8Hz, 11Hz), 6.72(1H, m), 6.81 (1H, d, J=2Hz), 6.84(1H, d, J=8Hz), 6.86(1H, d, J=3Hz), 6.96(1H, dd, J= 3Hz, 5Hz), 7.26(1H, d, J=5Hz) |
| 70 | trans | 2-F | $CH_2$ | 2-F,3-OH-phenyl | Br | amorphouse | $C_{17}H_{17}F_2NO_3 \cdot HBr$ | H-NMR(400MHz, $D_2O$) δ; 2.79(1H, dd, J=8Hz, 14Hz), 3.02(1H, dd, J=6Hz, 14Hz), 3.08~3.20(1H, m), 3.28(1H, t, J= 11Hz), 3.36(1H, t, J=11Hz), 3.74~3.88(2H, m), 6.67 (1H, dd, J=1.5Hz, 7Hz), 6.71~6.82(3H, m), 6.93~7.02(2H, m) |

Example 71

Trans-(3,4-dihydroxyphenyl)-4-((2-hydroxy-3-methylphenyl)methyl)pyrrolidine hydrogen bromide was produced, being found to be amorphous and have C17H21NO3.HBr. NMR data is:

H-NMR (400 MHz; D2O) δ; 2.20(3H, S) 2.79(2H, dd, J=8 Hz, 7Hz) 2.86-2.97(1H, m) 3.11-3.19 (1H, m) 3.23 (1H, dd, J=10 Hz, 10 Hz) 3.28 (1H, dd, J=10 Hz, 10 Hz) 3.67 (1H, dd, J=8 Hz, 12 Hz) 3.78 (1H, dd, J=8 Hz, 12 Hz) 6.77-6.79 (2H, m) 6.84 (1H, dd, J=8 Hz, 12 Hz) 6.77-6.79 (2H, m) 6,84 (1H,dd, J=8 Hz, 8 Hz) 6.90 (1H, dd, J=2 Hz, 7 Hz) 6.99 (1H, dd, J=2 Hz, 7 Hz) 7.04 (1H, d, 7 Hz)

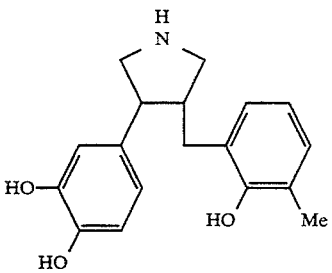

Example 72

The following five compounds were produced.
3-(3-chlorophenyl)-4-(3,4-dihydroxyphenyl)pyrroldine (1)
3-(3-bromophenyl)-4-(3,4-dihydroxyphenyl)pyrroldine (2)
3-(4-chlorophenyl)-4-(3,4-dihydroxyphenyl)pyrroldine (3)
3-(4-bromophenyl)-4-(3,4-dihydroxyphenyl)pyrroldine (4)
3-(3,4-dihydroxyphenyl)-4-(4-methylphenyl)-pyrrolidine (5)

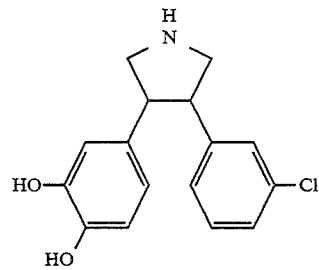
(1)

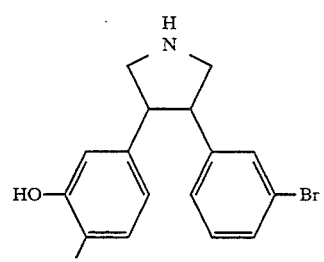
(2)

-continued

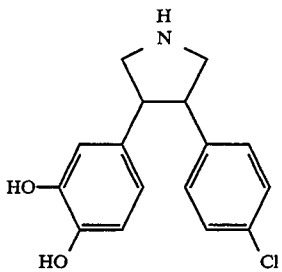
(3)

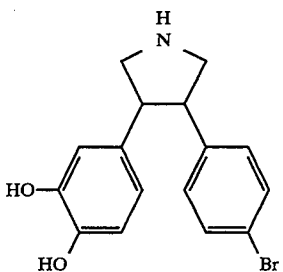
(4)

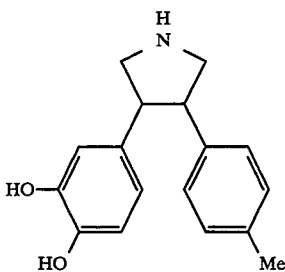
(5)

The last three compounds were obtained in the form of their hydrogen bromide salt. Their analytical data follow:

(3)
mp 184°–185 °C.
MASS: 290 (M+)
NMR(D₂O) δ: 3.23–3.47 (4H, m) 3.72 (1H, dd, J=11, 11 Hz) 3.74 (1H, dd, J=11, 11 Hz) 6.53 (1H, dd, J=2, 8 Hz) 6.63 (1H, d, J=2 Hz) 6.65 (1H, d, J=8 Hz) 7.09 (2H, d, J=8 Hz) 7.19 (2H, d, J=8 Hz)

(4)
mp 1.97°–199° C.
MASS: 334 (M+)
NMR(D₂O) δ: 3.26 (1H, dd, J=11, 11 Hz) 3.30 (1H, dd, J=11, 11 Hz) 3.37 (1H, dd, J=11, 11 Hz) 3.43 (1H, dd, J=11, 11 Hz) 3.71 (1H, dd, J=11, 11 Hz) 3.75 (1H, dd, J=11, 11 Hz) 6.53 (1H, dd, J=2, 8 Hz) 6.63 (1H, d, J=2 Hz) 6.65 (1H, d, J=8 Hz) 7.02 (2H, d, J=9 Hz) 7.33 (2H, d, J=9 Hz)

(5)
mp 190°–191 °C.
MASS: 270 (M+ +1)
NMR(D₂O) δ: 2.37 (3H, S) 3.52 (1H, dd, J=12, 12 Hz) 3.55 (1H, dd, J=12, 12 Hz) 3.64 (1H, dd, J=12, 12 Hz) 3.72 (1H, dd, J=12, 12 Hz), 3.96–4.02 (2H, m) 6.81 (1H, dd, J=2, 8 Hz) 6.91–6.93 (2H, m) 7.29 (4H, S)

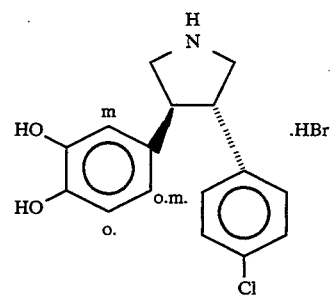
(3)

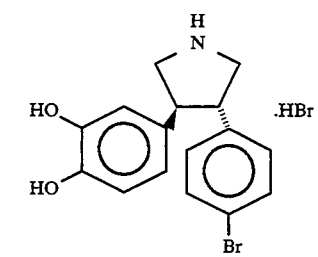
(4)

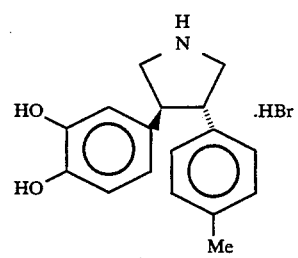
(5)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pyrrolidine compound having the formula or a pharmacologically acceptable salt thereof:

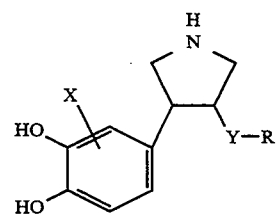

in which X is hydrogen, a halogen or a lower alkyl, Y is —(CH₂)$_n$—, n being zero, 1 or 2, and R is naphthyl, a substituted naphthyl wherein the substituents are selected from the group consisting of lower alkyl, lower alkoxy, halogen, hydroxy, and trifluoromethane, or a group of the formula:

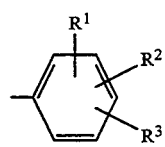

wherein R¹, R² and R³ are each independently a hydrogen, a lower alkyl, a lower alkoxy, a halogen, hydroxy, trifluoromethyl or —NR4R5, R4 and R5 are each hydrogen or a lower alkyl.

2. The pyrrolidine compound as claimed in claim 1, wherein Y is —(CH$_2$)$_n$— and n is zero.

3. The pyrrolidine compound as claimed in claim 1, wherein Y is —(CH$_2$)$_n$— and n is 1 or 2.

4. The pyrrolidine compound as claimed in claim 1, wherein R¹, R² and R³ are each independently hydrogen, a halogen, hydroxy or a lower alkyl.

5. The pyrrolidine compound as claimed in claim 1, wherein R¹, R² and R³ are each independently a hydrogen, a halogen, hydroxy or a lower alkyl, Y is —(CH$_2$)$_n$— and n is zero.

6. The pyrrolidine compound as claimed in claim 1 which is the compound 3-(2-chloro-3-hydroxyphenyl)-4-(3,4-dihydroxyphenyl)-pyrrolidine.

7. The pyrrolidine compound as claimed in claim 1, which is the compound (±)-trans-3-(2-chloro-3-hydroxyphenyl)-4-(3,4-dihydroxyphenyl)-pyrrolidine.

8. The pyrrolidine compound as claimed in claim 1, which is the compound (−)-trans-3-(2-chloro-3-hydroxyphenyl)-4-(3,4-dihydroxyphenyl)-pyrrolidine.

9. The pyrrolidine compound as claimed in claim 1, in which the compound is selected from the group consisting of:

3-(3,4-dihydroxyphenyl)-4-(2-methylphenyl)pyrrolidine 3-(2-chlorophenyl)-4-(3,4-dihydroxyphenyl)pyrrolidine 3-(2-chloro-3-hydroxyphenyl)-4-(3,4-dihydroxyphenyl)pyrrolidine 3-(3-chloro-6-hydroxyphenyl)-1-methyl-4-(3,4-dihydroxyphenyl)-pyrrolidine 3-(2,6-dihydroxyphenyl)methyl-4-(3,4-dihydroxyphenyl)pyrrolidine 3-(3-chloro-2,6-dihydroxyphenyl)-methyl-4-(3,4-dihydroxyphenyl)-pyrrolidine 3-(3,5-difluoro-2-hydroxyphenyl)-methyl-4-(3,4-dihydroxyphenyl)-pyrrolidine, and 3-(3-fluoro-2-hydroxyphenyl)methyl-4-(3,4-dihydroxyphenyl)pyrrolidine.

10. The pyrrolidine compound as claimed in claim 9, wherein said compound is in the trans-form.

11. The pyrrolidine compound as claimed in claim 1, wherein at least one of R¹, R², and R³ is a group selected from a lower alkyl, trifluoromethyl, a halogen, and hydroxy.

12. A pharmaceutical composition which comprises a therapeutically effective amount of the compound as defined in claim 1 and a pharmacologically acceptable carrier.

13. A method for treating or preventing a disease for which dopamine 1 agonist activity is effective, which comprises administering to a patient suffering from said disease a therapeutically or preventively effective amount of the compound or the salt as defined in claim 1.

14. A method for treating or preventing hypertension, which comprises administering to a patient suffering from hypertension a therapeutically or preventively effective amount of the compound as defined in claim 1.

15. A method for treating or preventing heart failure, which comprises administering to a patient suffering from heart failure a therapeutically or preventively effective amount of the compound as defined in claim 1.

* * * * *